(12) United States Patent
Dourdeville

(10) Patent No.: US 10,031,113 B2
(45) Date of Patent: Jul. 24, 2018

(54) LIQUID-CHROMATOGRAPHY APPARATUS HAVING DIFFUSION-BONDED TITANIUM COMPONENTS

(75) Inventor: Theodore A. Dourdeville, Marion, MA (US)

(73) Assignee: WATERS TECHNOLOGIES CORPORATION, Milford, MA (US)

( * ) Notice: Subject to any disclaimer, the term of this patent is extended or adjusted under 35 U.S.C. 154(b) by 1322 days.

(21) Appl. No.: 12/528,704

(22) PCT Filed: Feb. 28, 2008

(86) PCT No.: PCT/US2008/055349
§ 371 (c)(1),
(2), (4) Date: Feb. 11, 2010

(87) PCT Pub. No.: WO2008/106613
PCT Pub. Date: Sep. 4, 2008

(65) Prior Publication Data
US 2010/0171055 A1    Jul. 8, 2010

Related U.S. Application Data

(60) Provisional application No. 60/892,134, filed on Feb. 28, 2007, provisional application No. 60/951,860, filed on Jul. 25, 2007.

(51) Int. Cl.
*F16K 11/074* (2006.01)
*G01N 30/60* (2006.01)
*B23K 20/02* (2006.01)
*B23K 20/233* (2006.01)
*B23K 20/24* (2006.01)
(Continued)

(52) U.S. Cl.
CPC ......... *G01N 30/606* (2013.01); *B23K 20/023* (2013.01); *B23K 20/233* (2013.01); *B23K 20/24* (2013.01); *B23K 2201/14* (2013.01); *B23K 2203/14* (2013.01); *G01N 30/6095* (2013.01)

(58) Field of Classification Search
USPC .................................... 137/625.46, 625.47
See application file for complete search history.

(56) References Cited

U.S. PATENT DOCUMENTS 3,397,278 A    8/1968  Pomerantz
3,538,744 A *  11/1970 Karasek ...................... 73/23.39
(Continued)

FOREIGN PATENT DOCUMENTS

CN    1057866 A    1/1992
CN    1532545 A    9/2004
(Continued)

OTHER PUBLICATIONS http://en.wikipedia.org/wiki/Titanium [online], Chemical properties section, first paragraph [retreived on Nov. 14, 2012].*
(Continued)

*Primary Examiner* — John Fox
(74) *Attorney, Agent, or Firm* — Deborah M. Vernon; Womble Bond Dickinson (US) LLP

(57) ABSTRACT

An HPLC apparatus includes a heat exchanger formed from diffusion-bonded first and second titanium substrates. At least two conduits for counterflow are defined between the first and second substrates.

5 Claims, 20 Drawing Sheets

(51) Int. Cl.
    *B23K 101/14* (2006.01)
    *B23K 103/14* (2006.01)

(56) References Cited

U.S. PATENT DOCUMENTS

| | | | |
|---|---|---|---|
| 4,019,372 A | | 4/1977 | Parkell et al. |
| 4,019,373 A | | 4/1977 | Freeman et al. |
| 4,242,909 A | | 1/1981 | Gundelfinger |
| 4,284,352 A | | 8/1981 | Carson |
| 4,909,325 A | | 3/1990 | Hopmann |
| 5,250,263 A | * | 10/1993 | Manz ............... 422/81 |
| 5,271,427 A | * | 12/1993 | Berchem ............ 137/375 |
| 5,567,868 A | * | 10/1996 | Craig et al. .......... 73/23.42 |
| 5,792,943 A | | 8/1998 | Craig |
| 5,988,703 A | * | 11/1999 | Craig ............ 285/288.1 |
| 6,073,648 A | * | 6/2000 | Watson et al. ......... 137/375 |
| 6,227,034 B1 | * | 5/2001 | Trochesset ........... 73/23.42 |
| 6,382,035 B1 | | 5/2002 | Nichols |
| 6,467,354 B1 | | 10/2002 | Allen |
| 6,612,153 B2 | * | 9/2003 | White et al. .......... 73/23.42 |
| 6,672,502 B1 | | 1/2004 | Paul et al. |
| 6,748,975 B2 | * | 6/2004 | Hartshorne et al. ..... 137/625.46 |
| 6,783,871 B2 | | 8/2004 | Sheng |
| 6,811,916 B2 | | 11/2004 | Mallari et al. |
| 6,852,291 B1 | * | 2/2005 | Johnson et al. ........ 422/540 |
| 6,966,212 B2 | | 11/2005 | Klee et al. |
| 7,097,809 B2 | | 8/2006 | Van Dam et al. |
| 7,115,182 B2 | * | 10/2006 | Wei et al. ........... 156/272.2 |
| 7,566,396 B2 | * | 7/2009 | Iwata ............... 210/198.2 |
| 2001/0035516 A1 | | 11/2001 | Nichols et al. |
| 2003/0061867 A1 | | 4/2003 | Gerner et al. |
| 2004/0207074 A1 | * | 10/2004 | MacDonald et al. ...... 257/708 |
| 2004/0232366 A1 | | 11/2004 | Seeley |
| 2005/0161381 A1 | | 7/2005 | Norman |
| 2005/0165121 A1 | | 7/2005 | Wang et al. |
| 2005/0220681 A1 | | 10/2005 | Chang et al. |
| 2005/0223775 A1 | * | 10/2005 | Klee et al. ............. 73/23.41 |
| 2006/0038402 A1 | * | 2/2006 | Norman et al. .......... 285/384 |
| 2008/0142479 A1 | * | 6/2008 | Beerling et al. ......... 216/58 |

FOREIGN PATENT DOCUMENTS

| | | |
|---|---|---|
| EP | 0460872 A1 | 12/1991 |
| GB | 1281765 A | 7/1972 |
| JP | 01-245126 A | 9/1989 |
| JP | 2000320670 A | 11/2000 |
| JP | 2002-031040 A | 1/2002 |
| JP | 2004521320 A | 7/2004 |
| JP | 2005504969 A | 2/2005 |
| JP | 2005345279 A | 12/2005 |
| WO | 92/15830 A1 | 9/1992 |
| WO | 0239088 A1 | 5/2002 |
| WO | 03029809 A1 | 4/2003 |
| WO | 2006083776 A2 | 8/2006 |

OTHER PUBLICATIONS

Schubert, K., et al., "Microstructure Devices for Applications in Thermal and Chemical Process Engineering," Microscale Thermophysical Engineering, vol. 5, 2001, pp. 17-39.

Qin, Kuide, et al; A chemical mechanical polishing model incorporating both the chemical and mechanical effects; Science Direct, Thin Solid Films 446 (2004) pp. 277-286.

Wallis, G.; Direct-Current Polarization During Field-Assisted Glass-Metal Sealing; Presented at the 71st Annual Meeting, The American Ceramic Society, May 6, 1969, pp. 563-567.

Clark, E. J.; Vacuum Diffusion Joining of Titanium; Welding Research Supplement; pp. 251s-258s, Jun. 1959.

Sun, G., et al.,"The Designing and Experimental Investigating of a Sort of Rotary Cutting Valve", Liaoning Shihua University, Journal of Fushun Petroleum Institute, vol. 23, No. 1, pp. 49-52, Mar. 2003 (English Abstract provided).

\* cited by examiner

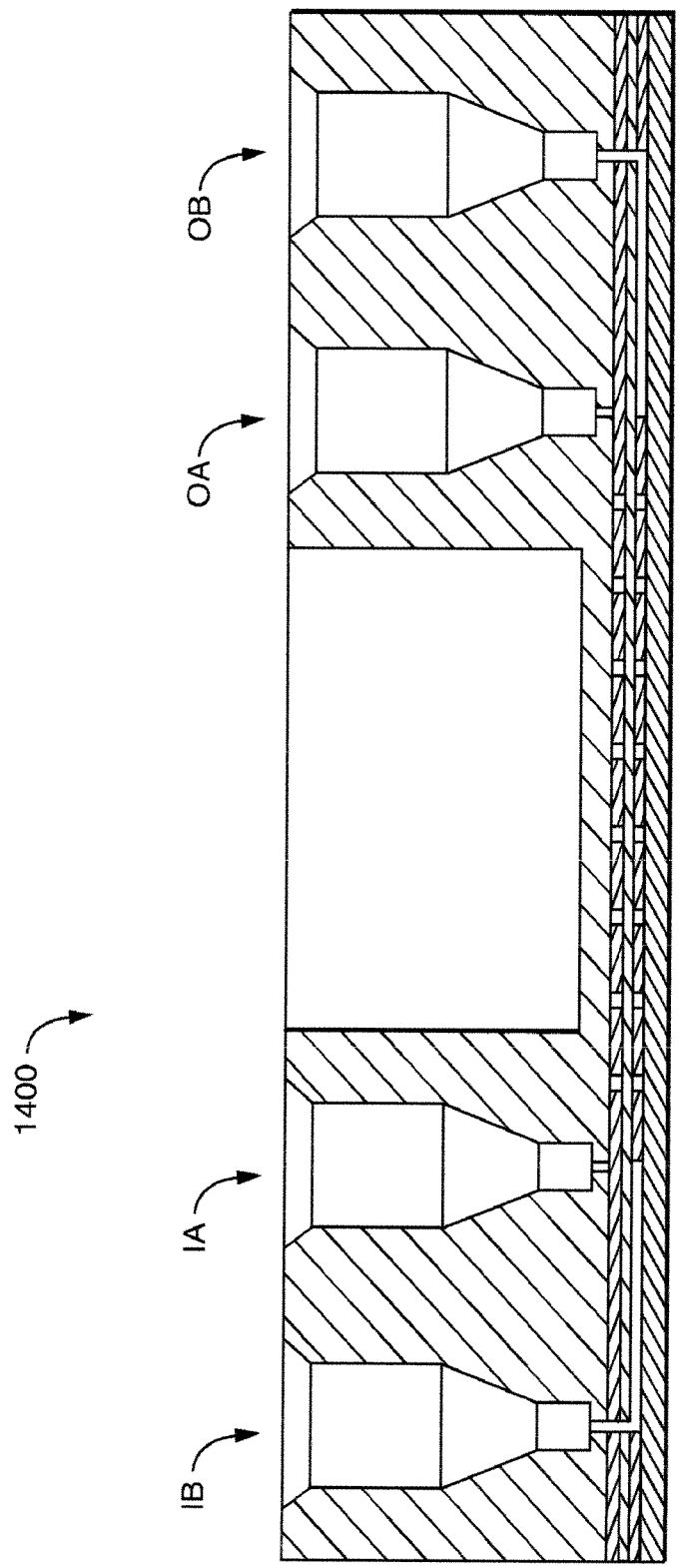

LIQUID-CHROMATOGRAPHY APPARATUS HAVING DIFFUSION-BONDED TITANIUM COMPONENTS

CROSS REFERENCE TO RELATED APPLICATIONS

This application is the National Stage of International Application No. PCT/US2008/055349, filed Feb. 28, 2008, which claims benefit of U.S. Provisional Application No. 60/892,134, filed Feb. 28, 2007, and U.S. Provisional Application No. 60/951,860, filed Jul. 25, 2007, the contents of which are incorporated herein by reference.

TECHNICAL FIELD

The invention generally relates to chromatography apparatus, and, in particular, high-pressure liquid-chromatography instruments.

BACKGROUND INFORMATION

A brief discussion of the volume-scale of chromatography and its effect on fluid-path implementation is given below. High-performance liquid chromatography (HPLC) is traditionally performed using analytical columns having a finished internal diameter (ID) or bore of about 4.6 mm, and a length typically in the range of about 5 cm to 25 cm. Such columns are typically assembled from carefully machined components.

The column tube typically has a male thread on each end, which engages a corresponding female thread within respective column end-fittings or terminals. Each column end-fitting incorporates features critical to the performance of the finished column. Among these features is a frit and diffuser plate, which cooperate to retain the particulate stationary phase (or packing) within the column bed, and to transition the liquid flow between the geometry of the narrow-bore input/output interconnect tubing (0.23 mm ID) and the much broader diametral dimension of the packed bed (4.6 mm.) Each column end-fitting also includes a threaded compression port, which is used to establish a substantially leak-tight interface between the column and an interconnect tube.

A traditional 4.6 mm ID HPLC column might be packed with a stationary phase incorporating a characteristic packing-particle diameter of 5 micrometers. Operation of that column at a suitable mobile-phase volumetric flow rate will result in a characteristic mobile-phase linear velocity through the bed structure. If the column is well-packed (i.e. in the substantial absence of voids, bridges, or other bed defects,) then this operating regime will result in a characteristic separation "efficiency" for this system, as demonstrated through the use of one or more types of probe compounds. The characteristic efficiency may be thought of as a measure of the narrowness of the chromatographic zones or bands which may be propagated through the system.

In an HPLC analytical instrument, it is generally desirable to perform separations with high efficiency, thereby maximizing information content of the chromatogram by enhancing the resolution of interfering or near-interfering zones or bands. A band which is eluted from the above-described system might be expected to have a time-course of substantially 10 seconds, measured at 5-sigma (i.e., passage of the concentration-distribution of the band through a detector, including the band apex, as well as 2.5-sigma of the band preceding and trailing the apex.)

With knowledge of the volumetric flow rate, one can convert the width of the band in time units to a width in volume units (167 microliters in this example, for a flow rate of 1.0 mL per minute. Working in the volume domain is particularly instructive as one proceeds to investigate the impact of "extra-column" volumes on the efficiency of the separation. The existence of volumes external to the column (for example, in transport tubing, in detectors, and in injectors) generally can only degrade the quality of a separation as delivered by a column.

The extra-column variance (variance=$sigma^2$) contribution is an extremely useful measure to illuminate how a specified separation will be degraded in the presence of one or more types of extra-column contributions, as the variances are substantially additive. It is instructive to tabulate the characteristic volume scale of several classes of chromatography systems, to perceive what the system designer is confronted with. In the tabulation below, the assumption is made that all systems will preserve the same efficiency value, and that mobile-phase linear velocity will be maintained constant through the packed bed. Thus, the volumetric flow rate has been scaled in proportion to column bed cross-sectional area, thus in proportion to column internal $radius^2$.

TABLE 1

| HPLC Scale | Column ID | Volumetric Flow Rate | Characteristic Peak Volume |
| --- | --- | --- | --- |
| Conv. Analytical | 3.9-4.6 mm | 1.0 mL/min | 167-200 uL |
| Narrow-bore | 2.0 mm | 250 uL/min | 40-50 uL |
| Microbore | 1.0 mm | 50-70 μL/min | 10-12 uL |
| Capillary | 0.30-0.50 mm | 5-12 μL/min | 1.5-2.5 uL |
| Nanoscale | 0.05-0.15 mm | 10's-100's nL/min | 10-40 nL |

The column and flow-rate ranges of Table 1 illustrate how conventional tubing and tubing-interfaces, which are quite satisfactory for use in conventional-scale HPLC (where characteristic peak volumes are a significant fraction of a milliliter,) are quickly outclassed in applications such as capillary-scale or nanoscale HPLC (where characteristic peak volumes are in the few-microliter to tens-of-nanoliters range, and thus the extra-column variance "budget" is essentially gone.) Stated another way, extra-column volumes and extra-column variances that are acceptable in the practice of conventional HPLC are generally inappropriate in the practice of capillary and nanoscale LC techniques. Indeed, capillary and nanoscale techniques are at the forefront of separations technology at this time, largely because of their suitability for interfacing with mass spectrometry, particularly where the available sample-mass for analysis is limited (sample-limited analysis.)

In practice, few if any manufacturers have demonstrated the ability to maintain separation efficiency across the orders-of-magnitude of characteristic peak volume recited in Table 1. Moreover, there is concurrently a trend toward the use of smaller packing particle size, to achieve yet-higher separation efficiency. This higher efficiency results in a further decrease in the volume of an eluting zone or band, further exacerbating problems with extracolumn effects. Planar fluid-circuit approaches to minimizing extra-column volume and extra-column variance seem appealing in their ability to consolidate function and produce relatively short routing paths, but to date the materials of construction (typically glass, plastics, or certain ceramics) have not permitted the devices to withstand the internal hydrostatic pressures typical of modern small-particle separations. These latter pressures may be tens of thousands of PSI at the column head, corresponding to the regime of very-high-pressure liquid chromatography (VHPLC.)

SUMMARY OF THE INVENTION

The invention arises, in part, from a realization that a partially or fully integrated microfluidic circuit for inclusion in a chemical-separation device such as a HPLC instrument, is advantageously fabricated, at least in part, from diffusion-bonded metallic layers. Titanium substrates, of a great variety of thicknesses, are particularly well suited for fabrication and operation of such instruments. Conveniently, in some exemplary embodiments of the invention, an HPLC instrument is fabricated, with various degrees of integration, from two or more laminated diffusion-bonded sheets of a titanium alloy. Other embodiments of interest, such as heat exchangers, valves, samplers, and/or pumps, are also based on diffusion-bonded titanium.

Some embodiments of the invention provide any or all of the following advantages: reduced length and/or numbers of sections of interconnect tubing, easier fabrication, lower-cost fabrication, improved ease-of-use of capillary-scale and nano-scale LC, reduced dead-volume, reduced size, disposable devices, integrated devices, small devices, and high-pressure liquid chromatography in diffusion-bonded monoliths at pressures in excess of about 5,000 psi or 10,000 psi, and as high as about 15,000 psi, or higher. Some embodiments of the invention provide nano-scale microfluidic HPLC instruments that offer similar ease-of-use and reliable operation to that of prior analytical-scale or microbore-scale instruments.

Some embodiments of the invention provide advantages over prior systems in which a separation column is a consumable. A microfluidic-based high-pressure column, according to these embodiments, employ one or more no-fitting interfaces to ensure that low dead-volume is preserved at such interfaces when a user replaces a column. For example, one embodiment includes a substrate that defines a trap column and a separation column connected within the substrate. Some of these embodiments also include some macro-scale fittings, which, however, would rarely be manipulated by typical users.

Accordingly, one embodiment of the invention features an HPLC apparatus that includes a heat exchanger formed from diffusion-bonded first and second titanium substrates. At least two conduits for counterflow are defined between the first and second substrates.

A second embodiment of the invention features a rotary-shear-seal valve that includes a stator assembly. The stator assembly includes an external-plumbing interface portion formed of titanium and a gasket of titanium that is diffusion bonded to the external-plumbing interface portion. The external-plumbing interface portion defines at least two tubing ports. The gasket defines a fluid circuit for each of the tubing ports, an outer end of each fluid circuit being in fluid communication with a corresponding one of the tubing ports.

A third embodiment of the invention features an HPLC apparatus. The apparatus includes a separation column and a flow cell. The flow cell includes a cell body that defines a flow channel, an inlet port to receive an eluent from the separation column, an outlet port, a window disposed adjacent to an inlet of the flow channel, and a gasket disposed between the window and the cell body. The gasket defines a fluid circuit that connects the inlet of the flow channel to the inlet port. The cell body and gasket are formed of titanium and are diffusion bonded.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

FIG. 11A is an overall side section view of the exchanger that provides all fluid ports on the same side of the exchanger, in accordance with one embodiment of the invention;

DETAILED DESCRIPTION

Figure 1:
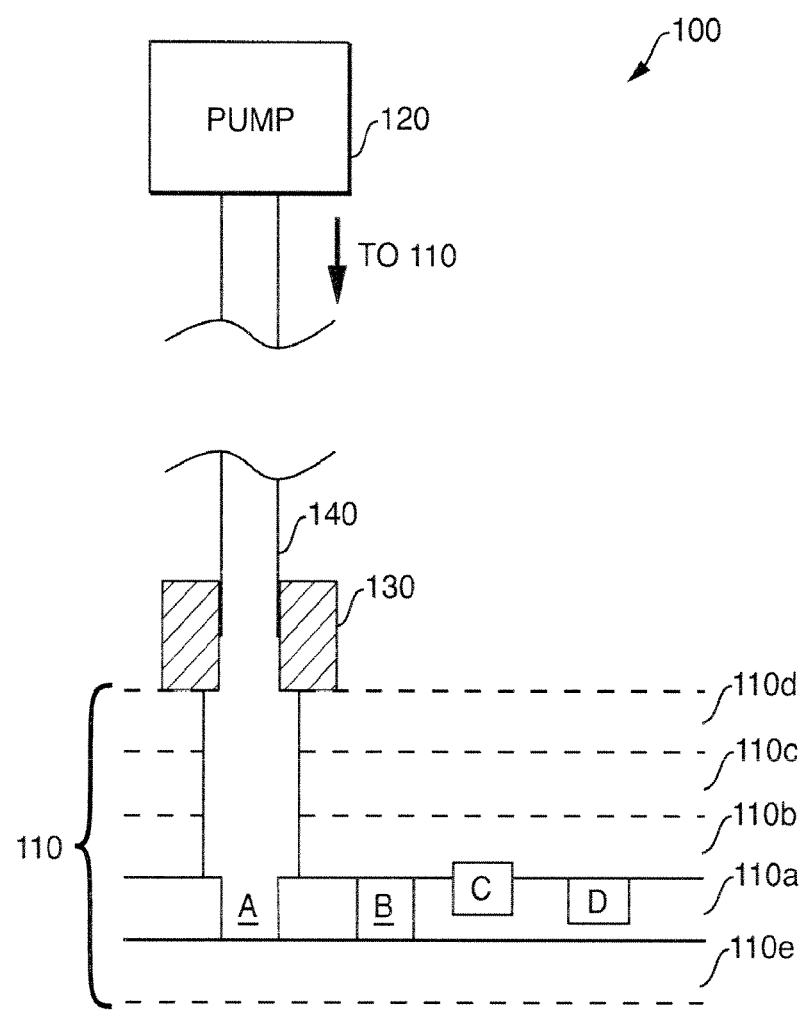
FIG. 1 is a side-view diagram of a portion of a chemical-processing device, in accordance with one embodiment of the invention.

The following detailed description, which includes some embodiments that entail particular materials and fabrication steps, is intended to be illustrative rather than comprehensive. Accordingly, this description should be understood as not limiting fabrication methods of the invention to any particular set of steps or particular materials.

"Diffusion bonding" herein refers to elevated-temperature processing that leads to direct bonding of substantially metallic components. Generally, heat and compressive stress are used in combination to urge two or more components together. In advance of the bonding step, lapping and polishing processes are optionally used to achieve mating surfaces that are extremely flat (typically to within some 10' s of millionths of an inch,) and which have a surface roughness statistic R_a in the vicinity of 2 to 4 millionths of an inch.

Assuming that diffusion bonding of metals entails atomic-level contact at faying surfaces, elevated temperature and a modest compressive stress (for example, a 500 to 1000 PSI global-mean stress) appear to enable the necessary intimate contact, by yielding the localized surface asperities which would otherwise tend to hold the faying surfaces apart. Given time at temperature, grain boundaries of the parent materials re-distribute so as to substantially eliminate evidence of the original bond-line.

Extensive testing of mechanical test-specimens by aerospace contractors indicates that the bond lines formed in titanium and alloys such as Ti 6Al-4V substantially retain the strength and durability of the parent materials. Titanium and alloys such as Ti 6Al-4V appear to be particularly well suited for vacuum diffusion bonding, as the base material appears readily capable of dissolving its own surface-oxide layer (passivation layer) at the bonding temperature. Thus one need not resort to unusual protocols in order to eliminate this passivation layer, and its effects upon the resulting bond. It will be recognized, however, that most metals can be diffusion bonded, when appropriate conditions are employed to deal with the passivation layer(s).

The diffusion bonding of like materials tends to produce a joint which is characterized by very low residual stress, which is in marked contrast to fusion welding techniques. In the diffusion bonding sequence for titanium, the faying surfaces are not taken to liquefaction. It is recognized that the temperatures involved (e.g., 840° C.) are sufficiently high to promote the yielding of local asperities. In most metals, an increase in temperature is commonly associated with a decrease in yield strength. As these local asperities respond to the highly-localized stress by yielding, the resulting applied-stress value tends to converge with the global mean compressive stress value, which substantially terminates further yielding. When proper conditions are employed, the diffusion bonding of two or more titanium substrates should result in substantially no net change in the dimensions of the parts, once the parts are returned to ambient temperature. This is useful because machined details such as compression ports can be introduced in the components at the time of initial machining, and those details will remain substantially accurate and useable following the bonding process.

By way of introduction, some preferred embodiments of the invention utilize two or more diffusion-bonded layers of metallic materials. The layers are optionally identical, similar and/or dissimilar. The layers optionally consist of substantially pure materials or alloys or composites that are suitable for diffusion bonding. A suitable diffusion bonding temperature is, for example, approximately 50% to approximately 70% or 90% of the melting temperature of the most fusible metal. Filler materials in metal-matrix composites are included to, for example, provide added strength and/or to control size and/or shape changes associated with temperature changes.

Diffusion bonding is performed in any suitable atmosphere or in vacuum. Some suitable atmospheres include inert gases, such as nitrogen, argon or helium. In some preferred embodiments of the invention, associated with a planar fluid circuit, the strength, stiffness, ductility, and fracture-toughness of an appropriately-selected structural metal allows that metal to perform well in a planar fluid circuit implementation where more-brittle materials would risk rupture, as the metal is capable of responding locally to a stress concentration without propagating a fracture that could destroy the device integrity.

Metallic layers are composed of any suitable materials, including known metallic materials. One suitable class of structural metals having the strength, stiffness, corrosion resistance, ductility, and fracture-toughness necessary to implement some high-pressure fluid circuits is the class of titanium alloys (including substantially pure titanium.) For example, some suitable titanium materials are available from Allegheny Technologies Inc.'s AllVac Division (Monroe, N.C.). These materials include: ALLVAC® 30, 40, 55, and 70 CP (commercially pure) titanium grades, which have different yield strengths associated with different oxygen levels; and ALLVAC® titanium 6Al-4V and 6Al-4V ELI alloy (includes about 6.3% Al, 3.8% V, and 0.017% Fe.) Certain forms of titanium which are not intentionally alloyed may be sold under the designation CP (for "commercially pure".) During diffusion bonding of titanium layers, in some embodiments, the titanium solubilizes its own oxide layer.

The following description focuses on preferred embodiments that include titanium diffusion-bonded components. Some principles of the invention are applicable, however, to diffusion-bonded components formed from other metals. The word "titanium" is used in the following to refer to both substantially pure titanium and suitable titanium alloys.

Suitable methods of forming fluid paths in high-pressure titanium-based fluid circuits include, for example, photochemical through-etching of thin sheets, or photochemical blind-etching of thicker sheets, of the metal material. Alternatively, the material removal required to generate fluid paths may be accomplished by electrochemical milling, laser ablation, laser ablation with oxygen gas feed, electrical discharge machining ("EDM"), focused ion beam ("FIB"), electron-beam cutting, reactive-ion dry etching, mechanical cutting, or any alternate suitable means.

A planar fluid path is optionally implemented substantially within a single through-etched thin layer or foil, which is optionally subsequently captured between two unetched facing layers. Alternatively, the fluid path may be implemented as a blind-etch in one material layer, or as mirror-image blind-etches constructed in two sheets of material which share a bond plane. If desired, a circuit could incorporate a fluid path which is through-etched in a central foil, in addition to blind-etched fluid path components residing in the facing sheets.

The fluid path may reside in a plurality of distinct layers, with vias used to interconnect between planes as desired, analogous to that that found in printed circuit board (PCB) construction. The metal facing sheets may be constructed with machined features which permit high-pressure fluid-tight connections (for example, via threaded compression ports) to be made to the bonded assembly, facilitating assimilation of the bonded assembly into realistic systems incorporating high-pressure pumps, sample injectors, detectors, etc., thereby overcoming one of the limitations of prior art planar fluid circuits implemented in other materials.

As a component of a high-pressure-capable separation system, an etched-and-bonded titanium fluid-path element optionally is used to encompass or implement any portion of a system for which it is deemed suitable, including a separation column packed with a stationary-phase, an in-line heat exchanger, a detector cell or cell component, a pump manifold, and/or a component of a sample injector, for example. The complete functionality of a separation system need not reside on a single etched-and-bonded device, but, rather, that functionality is optionally spread across multiple devices which have size- and internal-volume-scales, and circuit complexity, appropriate to their designated tasks.

Some appropriate methods of joining structural metals readily produce a high-pressure-capable, fluid-tight seal over the joining plane, without corrupting the fluid-path features lying within the joining plane, or immediately adjacent to it, and preferably without introducing or exposing secondary materials to the fluid path.

As indicated above, titanium and titanium alloys are joined, for example, by vacuum diffusion bonding. Any suitable diffusion-bonding process, including known processes, is optionally employed. Some suitable vacuum diffusion-bonding processes are presently utilized in the aerospace industry. Vacuum diffusion bonding permits appropriately-prepared titanium surfaces to be directly bonded under prescribed conditions which include, for example, provision of a controlled atmosphere, elevated temperature, compressive stress on a laminate stack, and time; such conditions generally do not require the use of an intervening filler metal or braze. Vacuum diffusion bonding of titanium and titanium alloys generally provides an integral component, in which grain boundaries of adjoining layers and/or grain boundaries formed at the interface(s) between layers have migrated so as to span the original bond plane or planes. When properly designed, a plurality of layers are optionally bonded at one time, within the context of one vacuum-furnace "oven run".

As one example, the above-mentioned Ti-6AL-4V alloy is optionally diffusion bonded with a nominal mean compressive stress of about 500 to 1000 PSI and with heating applied over the course of multiple hours, typically with a shallow linear ramp of temperature employed from the room-temperature condition to the bonding temperature condition, and from the bonding temperature condition back down to room temperature. The resulting trapezoidal temperature profile may entail two or more hours at the bonding temperature.

Preferably, the contacting layers have a good surface finish, for example, a surface roughness statistic $R\_a$ of 2 to 4 microinches or better, and a flatness or global planarity to within 20 to 40 microinches. Bonding occurs in any suitable environment, such as an inert gas, or a vacuum of $1.0 * 10^{-5}$ torr or better. Preferably, the environment is substantially free of oxygen.

Diffusion bonding of a stacked assembly converts the stack to bonded state, forming a substantially monolithic structure in which the originally distinct metallic layers are often no longer individually distinguishable. That is, an interface between layers (also referred to as a bond-plane) is replaced with a grain structure typical of the bulk material, such that the original bond plane is no longer visible.

As was described above, many of the ease-of-use and reliability issues in a nano-scale HPLC system arise from the difficulty in making low dead-volume interconnections. A microfluidic-based HPLC system has the potential of avoiding many of these issues. At least some HPLC components are constructed as microfluidic elements, and desirable interconnections are made between these elements via suitable microfluidic channels.

Some illustrative embodiments of the invention are described in more detail in the following. In view of this description, other embodiments and components will be apparent to one having ordinary skill in the chemical-separation arts.

FIG. 1 is a cross-sectional diagram of a portion of a chemical-processing device 100, according to one embodiment of the invention. The device 100 includes a processing unit 110, a high-pressure pump 120, a tube 140 receiving a fluid from the high-pressure pump 120, and a high-pressure connector 130 that attaches the conduit 140 to the processing unit 110.

The processing unit 110 is formed, at least in part, from diffusion-bonded titanium, and defines a separation column in fluidic communication with an inlet port of the processing unit 110. In a preferred embodiment, the pump 120 is configured to deliver a liquid including a solvent at a pressure at least sufficient for high-performance liquid chromatography. The high-pressure connector 130 is in physical communication with the inlet port to provide a substantially leak-free connection for the conduit 140 receiving the liquid delivered by the high-pressure pump 120. The device 100 optionally includes additionally components such as pump(s), conduit(s), column(s), electrical component(s), computer(s), etc., as will be recognized by one having ordinary skill in the chemical-processing arts.

The processing unit 110 includes a first layer 110a and includes one or more diffusion-bonded additional layers 110b, 110c, 110d, 110e. Preferably, two or more of the layers 110a, 110b, 110c, 110d, 110e of the processing unit 110 are formed of titanium.

The separation column and other conduits defined by the processing unit 110 optionally extend fully or partially through the thickness of one or more of the layers 110b, 110c, 110d, 110e, as illustrated in FIG. 1 at reference indicia A, B, C, and D (viewed end-on.) The conduits A, B, C, D are defined in metallic material by removing portions of one or more of the layers 110b, 110c, 110d, 110e, for example, by the as described above. As illustrated, one of the conduits A is fluidically connected by the high-pressure connector 130 to the tube 140.

The separation column has any suitable width, preferably less than about 500 µm. For higher-pressure operation, the width is preferably less than about 200 µm. The high-pressure pump 120 and the high-pressure connector 130 are configured for substantially leak-free operation at a pressure greater than about 1 kspi, or greater than about 2 kpsi, or greater than about 5 kpsi, or greater than about 10 kpsi, or greater than about 15 kpsi, or greater than about 20 kpsi. In particular, some preferred embodiments of the invention are capillary and nano-scale HPLC systems that provide advantageous fluidic connections in comparison with some prior high-pressure systems. Some embodiments of suitable connectors that support high-pressure operation are described in more detail with reference to FIG. 2.

Figure 2:
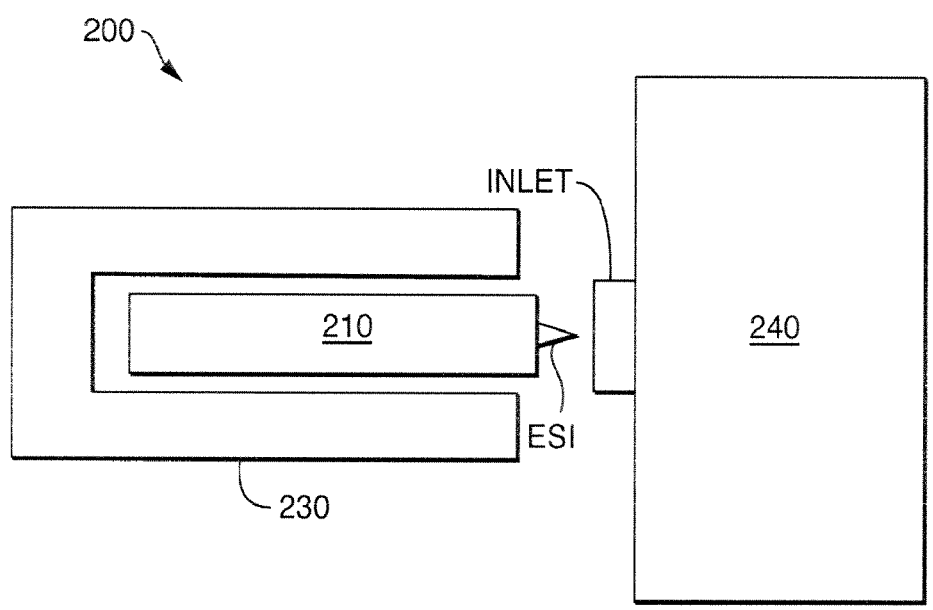
FIG. 2 is a side-view diagram of a portion of a liquid-chromatography instrument, in accordance with one embodiment of the invention.

FIG. 2 is a cross-sectional diagram of a portion of an instrument 200. The instrument 200 includes a processing unit 210, for example, similar to the unit 110, and a fixture 230. The instrument 200 optionally includes an analytical module 240, such as a mass-spectrometry unit, that provides further analysis of compounds outputted by the processing unit 210.

In alternative implementations, the fixture 230 acts as a support unit that, in part, positions the processing unit 210 adjacent to an inlet port of a mass spectrometer. In this implementation, the processing unit 210 optionally includes, for example, an electrospray interface (ESI) that directs separated material into the inlet port of the mass spectrometer. The ESI has any suitable configuration, which optionally includes features of configurations known to one having ordinary skill in the mass-spectrometry arts. Further details regarding embodiments of ESI's are described with reference to FIG. 6.

The fixture 230, in some alternative implementations, includes one or more hinges and/or one or more springs to facilitate disposition and exchange of processing units 210. The fixture 230 optionally includes components that interface with the processing unit 210b to provide, for example, fluidic and/or electrical connections to the processing unit 210. For example, in one alternative, the fixture 230 provides a fluidic connection to an inlet port of the processing unit 210.

In view of the above description, other configurations for the fixture 230 will be apparent to one having ordinary skill. For example, alternative fixtures support two or more processing units, and some instruments include two or more fixtures that support two or more processing units.

As indicated above, some preferred embodiments of the invention entail microfluidic-based instruments that support relatively high fluidic-pressures. In some embodiments of the invention, a separation column and/or other conduits are configured to sustain selected operating pressures, such as those required to perform HPLC. Column-configuration features of interest include, for example, dimensions and/or shapes that provide greater resistance to fracture failure under pressure loading or repeated pressure loading. Conduit configurations, such as height, width, aspect ratio, and/or radius of curvature are selected, for example, via empirical and/or theoretical considerations, as indicated above.

Figure 3:
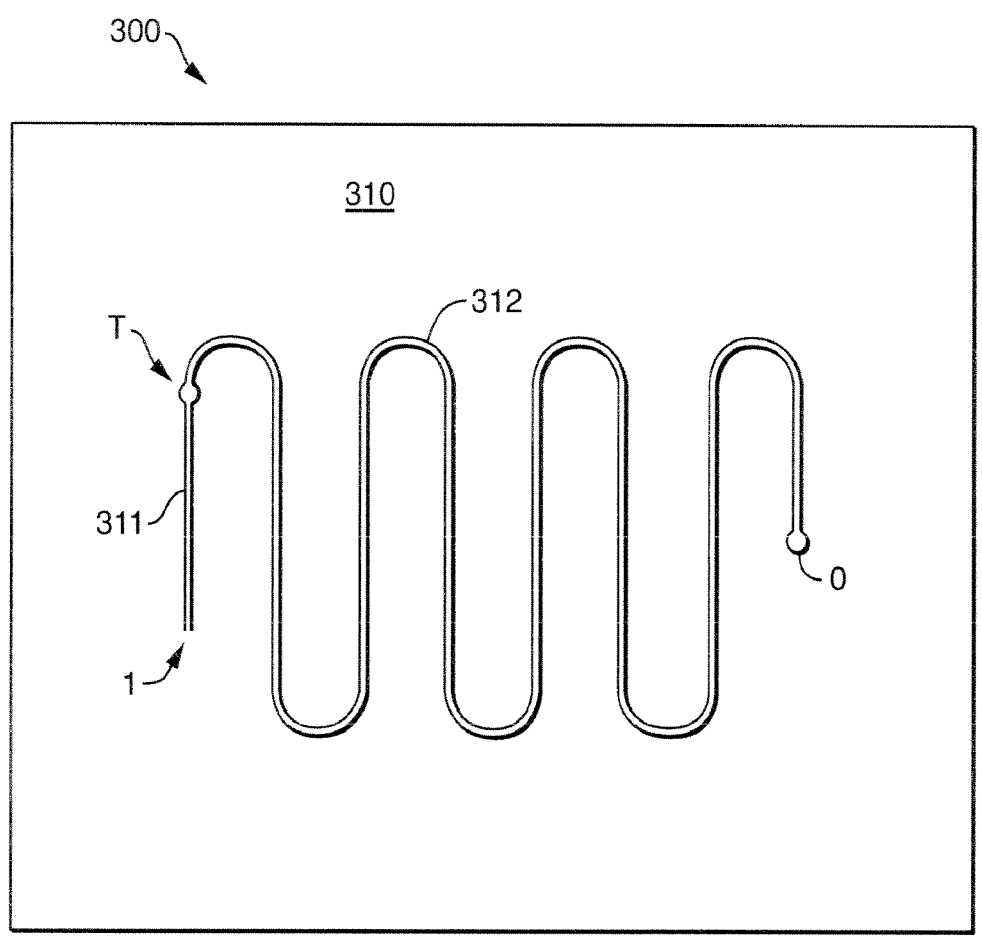
FIG. 3 is a top-view diagram of chemical-processing unit, in accordance with one embodiment of the invention.

FIG. 3 is a top-view diagram of chemical-processing unit 300, according to one embodiment of the invention. The unit 300 includes a diffusion-bonded titanium substrate 310 that defines a trap column 311, a separation column 312, and fluidic ports I, O, T including a trap-column inlet port I, a separation column outlet port O, and a trap-column outlet port T. The trap-column inlet port I provides an inlet to the trap column 311 for fluid from, for example, an injector and a pump. The trap-column outlet port T provides an outlet for the trap column 311. The separation-column outlet port O provides an output for an eluent exiting from the separation column 312.

In one alternative embodiment, a processing unit includes a three-layer titanium substrate. The bottom layer is a blank layer, the middle layer is a titanium foil that is patterned to define the trap and separation columns, similar to those depicted in FIG. 3, and the top layer has three via holes aligned with inlets and outlets of the trap column and the separation column, i.e., corresponding to the fluidic ports I, O, T of FIG. 3. The separation column has a serpentine configuration and a length of approximately 10 cm and a width of approximately 100 μm. The trap column has a length of approximately 1 cm and a width of approximately 180 μm. Generally, a serpentine or other non-linear column configuration permits a size reduction of a substrate for a given column length relative to a substrate or tube defining a substantially linear column.

A high-pressure fluidic connector is optionally attached, for example, via conventional means, to the trap-column inlet port. A connector is attached to the separation column outlet port, and a trap valve is attached to the trap-column outlet port.

The separation column is optionally slurry packed by attaching a fused-silica capillary to the outlet-port connector of the separation column; the capillary has a glass-particle frit to trap column-packing particles as a slurry flows through the separation column and out through the capillary. A dilution level of the packing slurry was empirically selected to provide good packing of the entire separation column. A separation column is optionally flushed and re-packed until a desired packing is obtained to, for example, obtain a desired chromatographic efficiency.

The chemical processing unit 300 is applicable, for example, to nano-scale HPLC with flow rates of less than 500 nL/min. As will be understood by one having ordinary skill in the chromatography arts, a large volume sample is loadable onto the trap column 311 at a flow rate of, for example, 5-20 uL/min. Once the sample has been loaded onto the trap column 311, the trap valve is closed and the solvent gradient is initiated, eluting the sample off the trap column 311 onto the separation column 312 for analysis.

The unit 300 reduces the number of tubing connections found in some prior nano-scale systems. The unit 300, in some alternatives, it used as a consumable due, in part, to its relatively low manufacturing cost.

Figure 4:
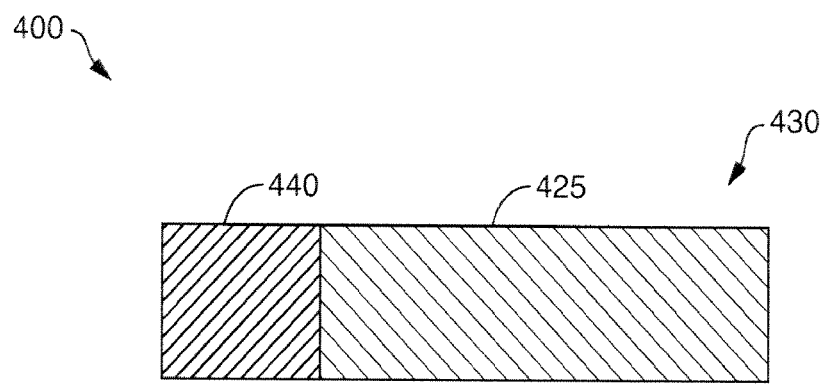
FIG. 4 is a block diagram of a top view of a portion of a titanium-based device, in accordance with one embodiment of the invention.
Figure 5:
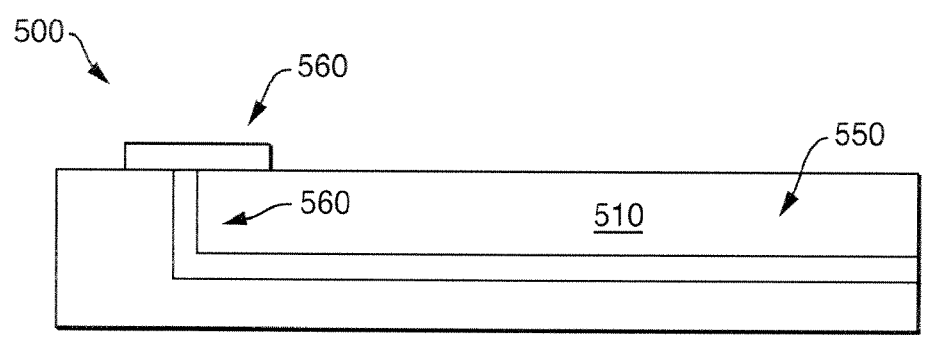
FIG. 5 is a block diagram of a side view of a portion of a titanium-based device 600c at an intermediate stage of fabrication, in accordance with one embodiment of the invention.

Referring next to FIGS. 4 and 5, some embodiments of the invention entail methods for packing conduits in titanium-based chromatographic devices. These embodiments include separation columns packed with, in some cases, spherical silica particles having diameters in a range of about 1-5 μm. The silica material is optionally derivatized with a variety of functional moieties to vary retention behavior.

Some of these embodiments make use of frits or other features to assist trapping of particles in a conduit, such as one or more separation columns. As described below, temporary and/or permanent structures disposed internally and/or externally to a substrate are used to trap particles, in some embodiments.

Some prior column packing techniques are not well suited to some metal-based nano- or capillary-scale chromatographic systems, according to some embodiments of the invention. For example, some prior high-temperature sintering and chemical bonding methods for frit creation require relatively easy access to the fritted area (i.e., to apply localized heating or deposition of chemical bonding agents.) Such easy access is not available in some embodiments.

FIG. 4 is a block diagram of a top view of a portion of a titanium-based device 400, according to one illustrative embodiment of the invention. The device 400 includes a separation column 430, a porous plug 440 disposed in the column 430, and packed particles 425 disposed in the column 430 adjacent to the plug 440. The porous plug 440 acts as a frit during packing of the column 430.

The porous plug 440 is fabricated via any suitable method, including known methods and methods described above. For example, the porous plug 440 originates from a paste deposited in one end of the separation column 430. The paste optionally includes material that becomes fixed via sintering and/or a chemical-bonding process.

FIG. 5 is a block diagram of a side view of a portion of a titanium-based device 600c at an intermediate stage of fabrication, according to another illustrative embodiment of the invention. The device 500 includes a substrate 510 defining a separation column and a via conduit connecting an end of the column to an outlet port, and a frit disposed to block the outlet port.

The frit includes any suitable material, including known materials. For example the frit is formed of filter paper, for example, an oriented filter paper that permits fluid flow in substantially a single direction.

The frit is permanently or removably attached to the substrate 510. The frit is attached to the substrate 510 via any suitable mechanism. For example, the frit is optionally glued and/or clipped to the substrate 510.

After packing of the column, the outlet port is optionally sealed with or without removal of the frit. For example the port and/or frit is optionally sealed with PDMS.

Figure 6:
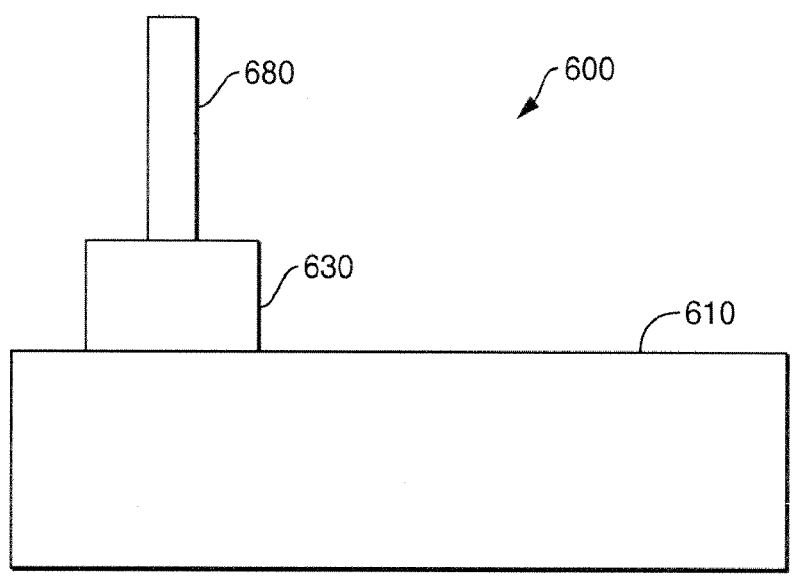
FIG. 6 is a block diagram of a side view of a portion a titanium-based device that includes a processing-unit and an electrospray interface, in accordance with one embodiment of the invention.

Next referring to FIG. 6, some embodiments of the invention involve electrospray interfaces for mass spectrometry. In some embodiments of the invention, such interfaces are an integral part of a titanium-based substrate or are attached to a titanium-based substrate. Some of these embodiments include replaceable electrospray tips. Some embodiments include two or more tips, such as an array of tips.

FIG. 6 is a block diagram of a side view of a portion a titanium-based device 600 that includes a processing-unit 610, an electrospray interface 680, and a connector 630. The electrospray interface 680 is permanently attached or removably attached to the substrate 610. The interface 680 is any suitable electrospray interface, including known interfaces. For example, the interface 680 optionally has a configuration that is similar to that of electrospray interfaces known to one having ordinary skill in the liquid-chromatography/mass-spectrometry interface arts.

Nano-scale HPLC components of some embodiments of the invention are preferably coupled to a mass spectrometer. A typical mass spectrometer is a concentration-sensitive detection technique that typically improves in sensitivity when flows of less than approximately 10 µL/min are used. While UV and fluorescence detection are major detection methods for analytical and microbore-scale chromatography, it is typically difficult to construct an optical detection flow cell with a low enough volume to prevent band broadening at flow rates of less than approximately 1 µL/min.

Figure 7:
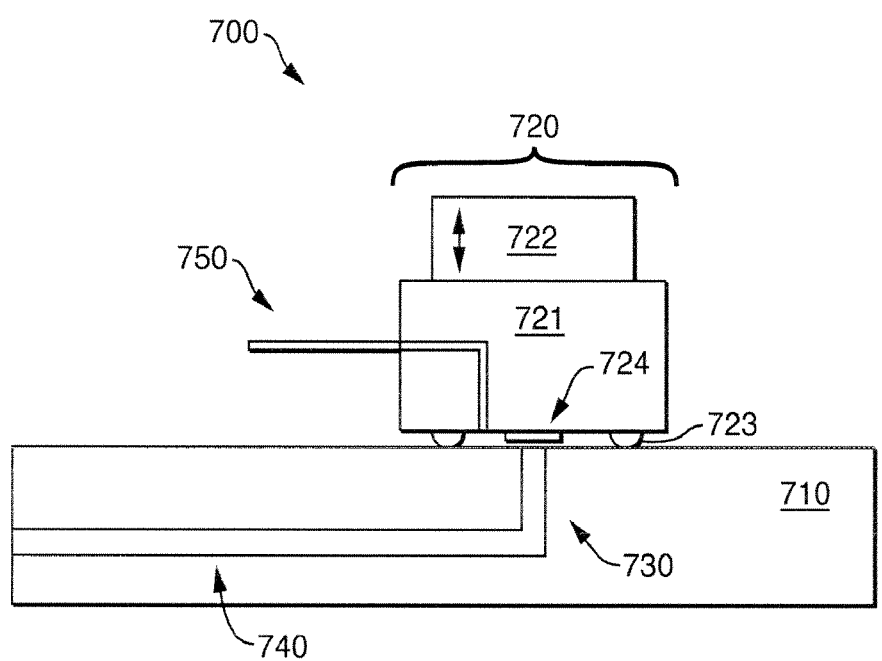
FIG. 7 is a block diagram of a side view of a portion of a titanium-based device, in accordance with one embodiment of the invention.

FIG. 7 is a block diagram of a side view of a portion of a titanium-based device 700, according to one illustrative embodiment of the invention. The device 700 includes a process-unit substrate 710 that defines a separation column, a trap column, and a fluidic via, similar to the embodiment illustrated in FIG. 3. The device 700 also includes a trap valve 720 in communication with an outlet port of the fluidic via.

The valve 720 includes a housing 721, a compliant member 723 that is directly or indirectly mounted on the housing 721, and an actuator 722 that is directly or indirectly mounted on the housing 721. The housing 721 defines a fluidic channel connecting fluidic ports to provide a pathway for a fluid flow entering and exiting the valve 720. The valve 720 is disposed adjacent to the outlet of the fluidic via.

The valve 720 has opened and closed states. In the closed state, the housing of the valve 720 or an optional component attached thereto blocks the outlet via port. For example, as illustrated, the valve 720 optionally includes a sealing component 724 that presses over and seals the outlet port when the valve 720 is in the closed state. When in the opened state, the compliant member 723 substantially prevent fluid from leaking away from the valve 720 rather than exiting, as desired, through the valve conduit.

In association with the variable valve state, the position of the housing 721 relative to the substrate 710 is adjustable in response to the actuator 722. As illustrated, the valve 720 is in an opened state The compliant member 723 preferably has an elastic property that permits it to recoverably deform and to provide a seal in spite of at least some particle(s) lodging between the compliant member 723 and the substrate 710.

The compliant member 723 has a circular configuration. In alternative embodiments, a compliant member has alternative configurations, for example, square, rectangular, or a more general shape. Moreover, a compliant member may include two or more component parts. As will be understood by one of ordinary skill, a compliant member may be, for example, an O-ring or a gasket.

At least a portion of the compliant member 723 includes a suitable compliant material(s), including, for example, a known compliant material. For example, an O-ring is suitably made from, for example, nitrile, silicone, fluorocarbon, fluorosilicone, ethylene propylene, neoprene, or polyurethane. In some embodiments, a compliant material is chosen for biocompatibility.

The sealing component 724 is formed of any material that suitably provides a fluidic seal when in contact with the via outlet port. The material is optionally chosen for biocompatibility and/or high-pressure performance. The sealing component, for example, provides a substantially leak-free seal at pressures up to about 1 kpsi, to about 2 kpsi, to about 10 kpsi, to about 15 kpsi, or higher.

The actuator 722 has any suitable configuration that permits controllable positioning of the housing 721 relative to the substrate 720. For the example, the actuator 722 optionally includes a piezo-electric material whose thickness varies via application of an electrical voltage. A piezo-electric actuator includes any suitable piezo-electric materials, including known materials.

Thus, in one example, expansion of a piezo-electric actuator leads to blocking of the outlet port, creating a high-pressure seal. Contraction of the piezo-electric actuator opens the high-pressure seal, allowing fluid to flow out of the port and through the valve conduit. A relatively low-pressure compliant member 723 ensures that fluid exiting the via port is directed out of a vent port of the valve 720.

The trap valve 720 controls diversion of flow to waste, thus enabling samples to be loaded onto the trap column at high flow rates. When the trap valve 720 is closed, flow is directed through the separation column.

Figure 8:
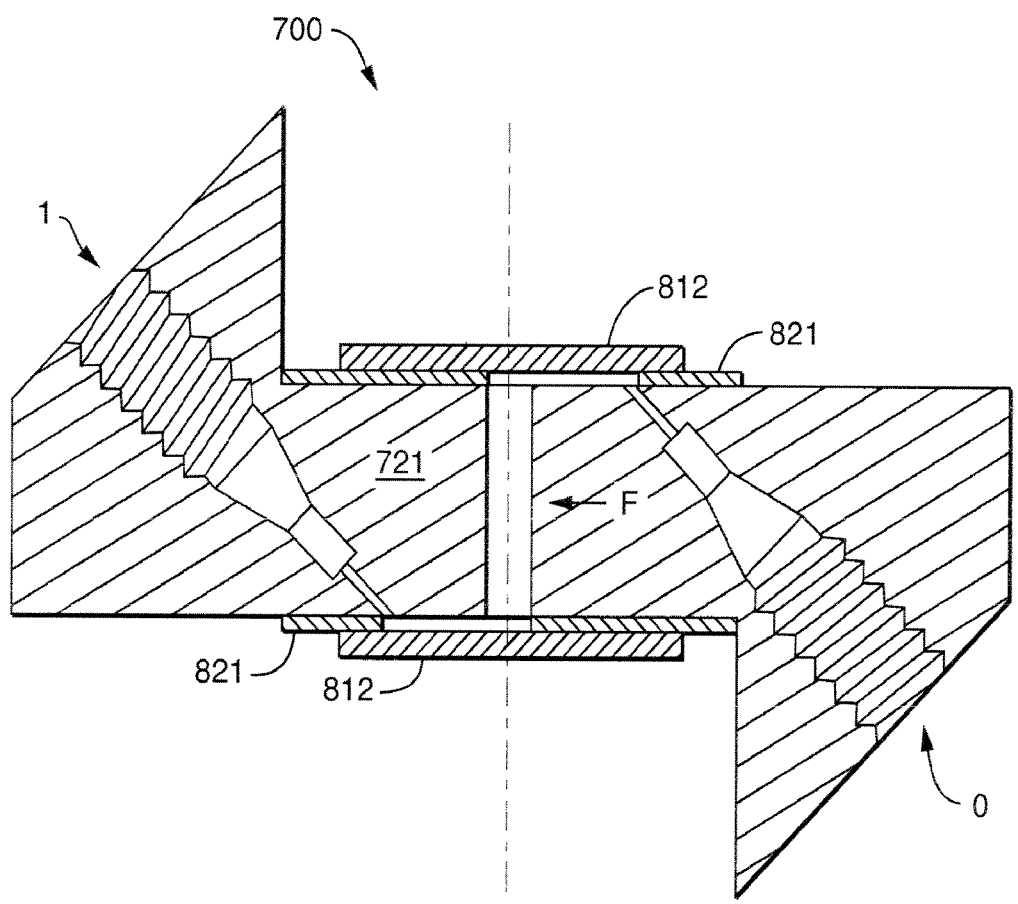
FIG. 8 is a side section diagram of a flow cell, in accordance with one embodiment of the invention.

FIG. 8 is a side section diagram of a flow cell 800, according to one embodiment of the invention. The flow cell 800 includes a cell body 810, two windows 811, 812, two gaskets 821, 822. The cell body 910 is formed of titanium and defines a flow channel F, an inlet port I to receive an eluent from a separation column, and a outlet port O. The windows 811, 812 are disposed adjacent to either end of the flow channel F to contain a fluid with the cell body 810 and to permit the passage of light for light-based analyses of the fluid in the channel F. In some implementations, the inlet and outlet ports I, O are compression ports (as illustrated,) as will be understood by one having ordinary skill in the chromatography arts.

The gaskets 821, 822, formed of titanium, are disposed between the windows 811, 812 and the cell body 810. The gaskets 821, 822 define fluid circuits that, respectively, connect the inlet and outlet ports I, O to either end of the channel F.

The gaskets 821, 822 are diffusion bonded to the cell body 810. The windows 811, 812 are diffusion bonded to the gaskets 821, 822. In this case, for example, regions of the sapphire window and the titanium gasket are provided with a chromium thin-layer, supplied by electron-beam evaporation of chromium in vacuum. The chromium layer provides an adhesion-promoting or linking-layer, to enhance the adhesion of an overcoated, thicker layer of gold (also deposited by electron-beam evaporation in vacuum.) In the subsequent diffusion-bonding process, it is a gold-gold diffusion bond which adheres the window material to the gasket, and thus to the cell body. This bond can be made at relatively low temperatures, which is helpful in avoiding residual stresses arising from the properties of the differing materials being bonded together.

Some embodiments of a HPCL apparatus include the flow cell 800 and optionally include light emitters and/or light detectors that work in cooperation with the flow cell 800. A detector includes, for example, a multi-channel detector, such as a charge-coupled device (CCD) or a photodiode array. The flow cell 800 thus supports, for example, light absorption and/or emission spectroscopy, as will be understood by one having ordinary skill in the chromatographic arts.

Thus, some embodiments of the invention integrate one or more windows with a diffusion-bonded component or components to provide, for example, observations of a fluid in the component(s).

Diffusion bonding of a multi-component (e.g. laminated) titanium assembly, as described above, is a highly effective technique for producing nanoscale, microscale, or analytical-scale fluid circuits for chromatography, in accordance with several embodiments of the invention. The fluid circuits so formed, in accordance with some embodiments, are capable of withstanding elevated internal hydrostatic pressures (corresponding to typical column head pressures observed in HPLC practice and greater pressures) due, for example, to a set of desirable materials properties (such as yield strength, ductility, fracture-toughness, and corrosion resistance.) With reasonable care the diffusion-bonding process substantially preserves these materials properties in the bonded specimen.

In nanoscale and microscale chromatography applications, in some embodiments, an analyte-detector interface is substantially co-located with a column exit, such that, for example, extra-column zone or band broadening is minimized. In prior-art systems addressed to conventional-scale chromatography, it is typical for a modular detector apparatus to interface with the column exit by way of a length of discrete tubing or plumbing which enables the transport of analyte between those two locations which may be separated by a distance of several tens of centimeters, or more. The volume of the eluting zones or bands in conventional-scale chromatography is sufficiently large that this arrangement is generally practicable at that scale, given the use of sufficiently narrow-bore interconnect tubing.

However, as the scale of chromatography is reduced to that of microscale or nanoscale separations, the extra-column volume which can be afforded for analyte transport becomes correspondingly small. At such reduced volume scales, a detector interface is desireably substantially integrated directly with a column exit. In the case of an ESI to a mass spectrometer, this substantially direct integration, in some embodiments, corresponds to the provision of an electrospray cone or tip on the microfluidic circuit which implements the column. In the case of an optical detection technique, such as ultraviolet (UV) absorbance detection, or fluorescence detection, substantially direct integration, in some embodiments, corresponds to the provision of a window for optical interrogation of the chromatography eluent, located immediately downstream of the column exit. Additional non-wetted optical elements, as known from prior art optical detectors, are used, in some embodiments, to select and direct components of an optical beam toward and from the windowed region of a flow path.

Thus, some embodiments of the invention entail provision of windowing to support optical detection integrated with the analytical column exit. Although the following description refers to a single column and particular types of columns, one of skill will recognize that alternative embodiments of the invention include multiple columns and/or alternative locations for a window or windows.

By definition, analyte detection at the column exit occurs downstream of the analytical column, and hence downstream of the principal fluidic resistance in the system. Therefore, the drive pressure which exists at the column head to create and sustain the analytical column flow is substantially dissipated at the point in the fluid circuit where analyte detection is to occur. This is fortuitous, as some techniques for integration of optical windows into the flow path, according to some embodiments of the invention, do not achieve the same operating pressure specification as that associated with the diffusion bonding of titanium to titanium elsewhere within the fluid circuit structure. Windows, in some embodiments, are constructed from more brittle materials, and those materials, in some cases, have differing coefficients of thermal expansion from that of the underlying titanium structure.

Nevertheless, a leak-free and volume-efficient (i.e., substantially negligible volume) interface preferably is established between the windowed region and the surrounding fluid circuit structure. Optimally, that interface is capable of being cleanly and smoothly swept by the chromatography flow, and, also optimally, that interface avoids bulky clamping apparatus and a compliant (elastomeric or other relatively soft) gasketing layer. Compliant gaskets, in some instances, are troublesome, because the clamping pressure needed to ensure a fluid-tight seal, over time, causes the gasket material to distort into the fluid path, thereby violating the design intent of providing a fluid path which is very cleanly swept by the chromatography flow. Indeed, three of the noteworthy benefits of diffusion bonding of titanium fluid circuit elements are that: (1) a fully leak-tight seal is established where required; (2) no residual clamping apparatus is needed on the finished, bonded assembly, and (3) no soft gaskets are present which potentially extrude into, and cause blockage or disruption of, the flow path over time.

For some embodiments, with proper preparation, the titanium structure from which the column and other chromatographic components are fabricated, in planar form, lends itself to the bonding of substantially optically-transparent windows thereto, where such windows are constructed from wavelength-appropriate materials. Such materials optionally include, for example, glasses (including borosilicate compositions), fused silica (high-purity synthetic $SiO_2$), quartz (from naturally-occurring $SiO_2$), or sapphire ($Al_2O_3$), depending upon the application.

In one embodiment, involving fabrication of a device including a bonded window, preparation of the titanium includes planarization of the bonding surface, to reduce or substantially eliminate the surface asperities present at any of several length scales. Planarization techniques for silicon and for specific metals and dielectrics are known from the semiconductor fabrication industry. Chemical mechanical planarization (CMP) is one such technique of fundamental importance to the semiconductor industry, and has been the subject of numerous studies and several modeling efforts directed to a narrow range of commercially-relevant substrates.

CMP entails the favorable cooperative interaction of two mechanisms: (1) a chemical "softening" of a surface layer of the substrate caused by the selected slurry chemistry, and (2) removal of the "softened" surface material by mechanical interaction with a free-abrasive or a bonded abrasive, as selected by the operator. Removal of deposited-metal overburden layers is one of the purposes to which CMP is put in the semiconductor industry. In that application, the chemistry of "softening" may be tuned to achieve disproportionate material removal rates of two or more selected materials, for example, to achieve an intended "stopping" behavior in the process. In the planarization of a titanium fluid circuit component as a precursor to bonding, in some embodiments only a single substrate material is present, and it is present in sufficient depth such that achievement of a "stopping" behavior is not a primary consideration. CMP is discussed herein because of the quality of the planar surface which can be generated. Very fine aluminum-oxide free-abrasive particles (typically descending to 0.02 to 0.05 micrometers mean diameter within the polishing sequence) acting upon a partially-softened surface layer, optionally provide smooth, planar surfaces substantially devoid of "plowing-type" scratches or asperities.

The window or mating part to the titanium component preferably is finished to an optical-quality smooth and flat condition on at least one side. Any suitable finishing method is optionally employed, including known methods. For example, the optical finishing optionally is a conventional mechanical polish as opposed to a chemically-assisted or CMP process. In some embodiments, the window itself is part of a lensing system (such as a plano-convex lens element) which directs the optical beam, or is simply a planar structure intended to enclose and define a region of the fluid path in a manner which supports optical interrogation of the chromatography stream.

Some embodiments utilize bonding of appropriate glassy or ceramic inorganic materials such as glass, quartz, sapphire, or alumina to a metal (e.g., titanium) having appropriate surface finishes. Any suitable bonding method is optionally employed, including known methods.

Titanium is one of a group of metals preferentially used to achieve bonding to glassy or ceramic materials, in accordance with some embodiments of the invention. The titanium surface to be bonded optionally is substantially pure titanium metal, or may include a surface layer(s) such as an oxide or nitride. In practice, the range of materials to which titanium is bonded is dictated, in some cases, by the extent of matching of the respective coefficients of thermal expansion, as some known bonding methods involve temperatures elevated by several hundred degrees Centigrade over room temperature. Too great a mismatch in coefficient of thermal expansion of the bonded substrates potentially ruptures the bond as the material pair is cooled back to room temperature, or to a typical operating temperature which, in some cases, is well-removed from the bonding temperature.

When restored to substantially room temperature, an assembly containing a window which is properly bonded to a titanium microfluidic circuit substrate potentially remains liquid-tight in the presence of internal hydrostatic pressures as high as several hundred kilopascals or higher. While this pressure-withstanding capability is significantly less than that achieved with titanium-to-titanium diffusion bonding, it is sufficient to address analyte detection applications downstream of an analytical column, within a typical HPLC or higher-pressure microfluidic system configuration. As with diffusion bonding, soft gasketing layers and external clamping apparatus are advantageously avoided, affording a compact, leak-tight, and volume-efficient fluidic structure.

Next, some additional illustrative embodiments of components of separation systems, according to some principles of the invention, are described with reference to FIGS. 9 through 17.

FIGS. 9A-G are diagrams that illustrate various portions of a low-volume heat exchanger formed from diffusion-bonded titanium, in accordance with one embodiment of the invention. The exchanger is used to heat a fluid prior to a separating process. For example, the exchanger is optionally used upstream of a separation column implemented as a tube or in a titanium diffusion-bonded substrate. For example, the exchanger is optionally used immediately upstream of a narrow-bore ACQUITY® column (available from Waters Corporation, Milford, Mass.)

Figure 9A:
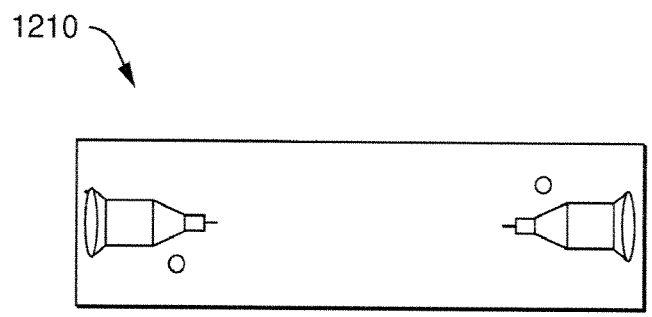
FIG. 9A is a top view of a foundation block of a low-volume heat exchanger, in accordance with one embodiment of the invention.
Figure 9B:
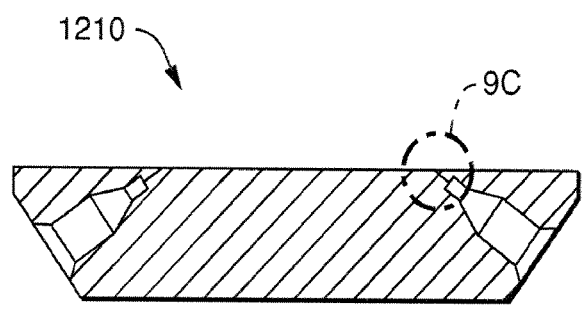
FIG. 9B is a side cross section of the foundation block of FIG. 9A.
Figure 9C:
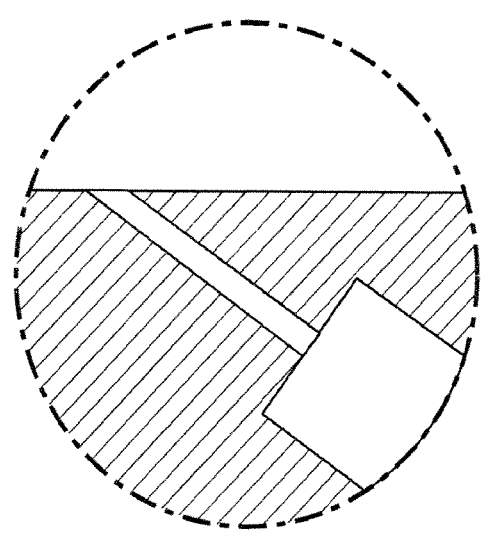
FIG. 9C is a detail of a port illustrated in FIG. 9B.
Figure 9D:
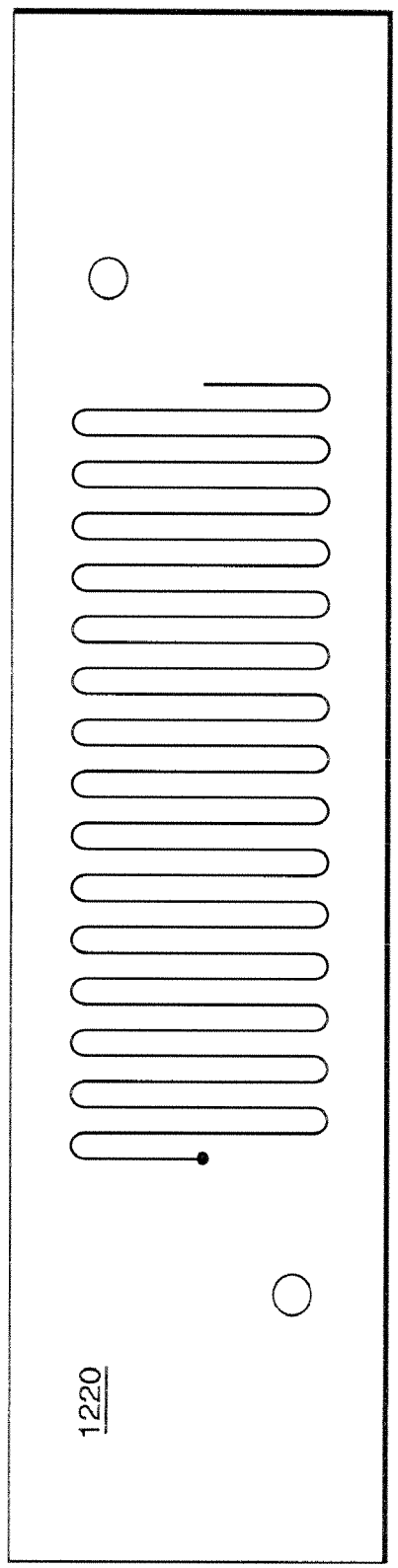
FIG. 9D is a top view of an planar portion of the low-volume heat exchanger, associated with FIG. 9A.
Figure 9E:
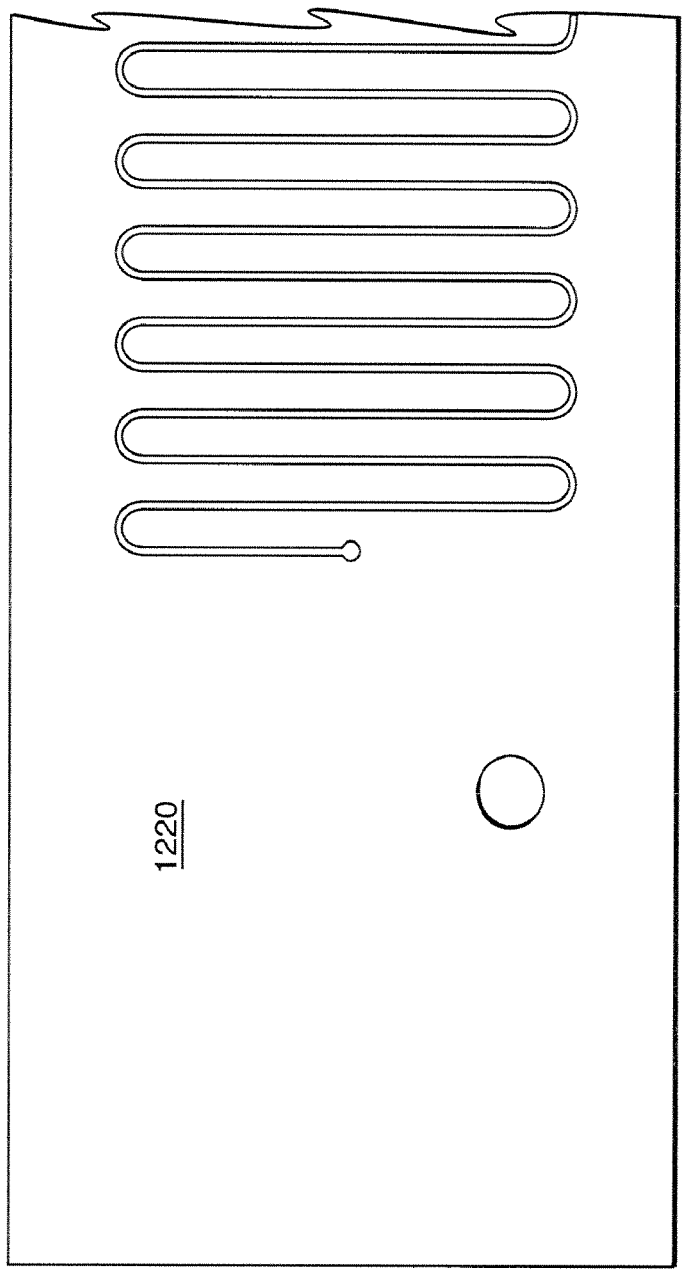
FIG. 9E is a more detailed view associated with FIG. 9D.
Figure 9F:
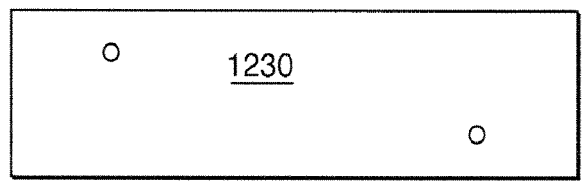
FIG. 9F is a top view of an upper capping plate of the low-volume heat exchanger, associated with FIG. 9A.
Figure 9G:
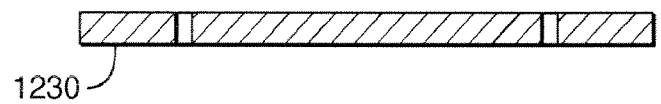
FIG. 9G is a side cross-section view of the plate of FIG. 9F.

The heat exchanger includes a foundation block 1210 (FIG. 9A, top view, FIG. 9B, side cross section, FIG. 9C detail of a port), a planar portion 1220 that defines a serpentine fluid path (FIG. 9D, top view, FIG. 9E, top view detail), and an upper capping plate 1230 (FIG. 9F, top view, FIG. 9G, side cross section.) The three illustrated components are preferably formed from titanium, and joined, via diffusion bonding, to form a single component.

The foundation block 1210 includes inlet and outlet compression ports O, I. The ports O, I are connected, via throughholes, to inlet and outlet ends defined by the serpentine fluid path. The components include optional alignment holes, to assist alignment of the throughholes in the foundation block 1210 with the inlet and outlet ends of the serpentine fluid path. The heat exchanger has a relatively extremely low internal volume and provides correspondingly low bandspreading.

Figure 10A:
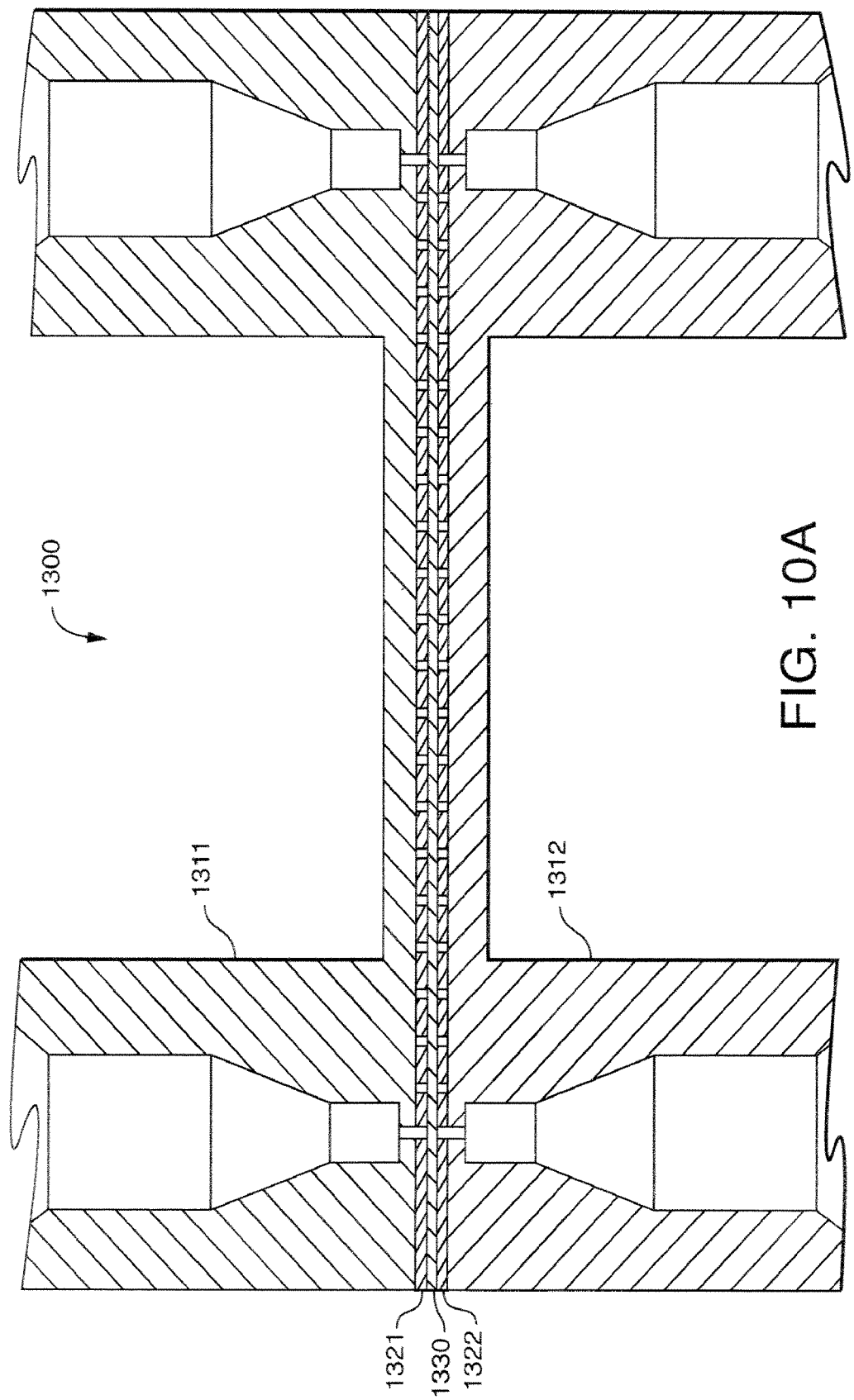
FIG. 10A is an overall side section view of the exchanger that provides fluid ports, for two fluid paths, on opposite sides of the exchanger, in accordance with one embodiment of the invention.
Figure 10B:
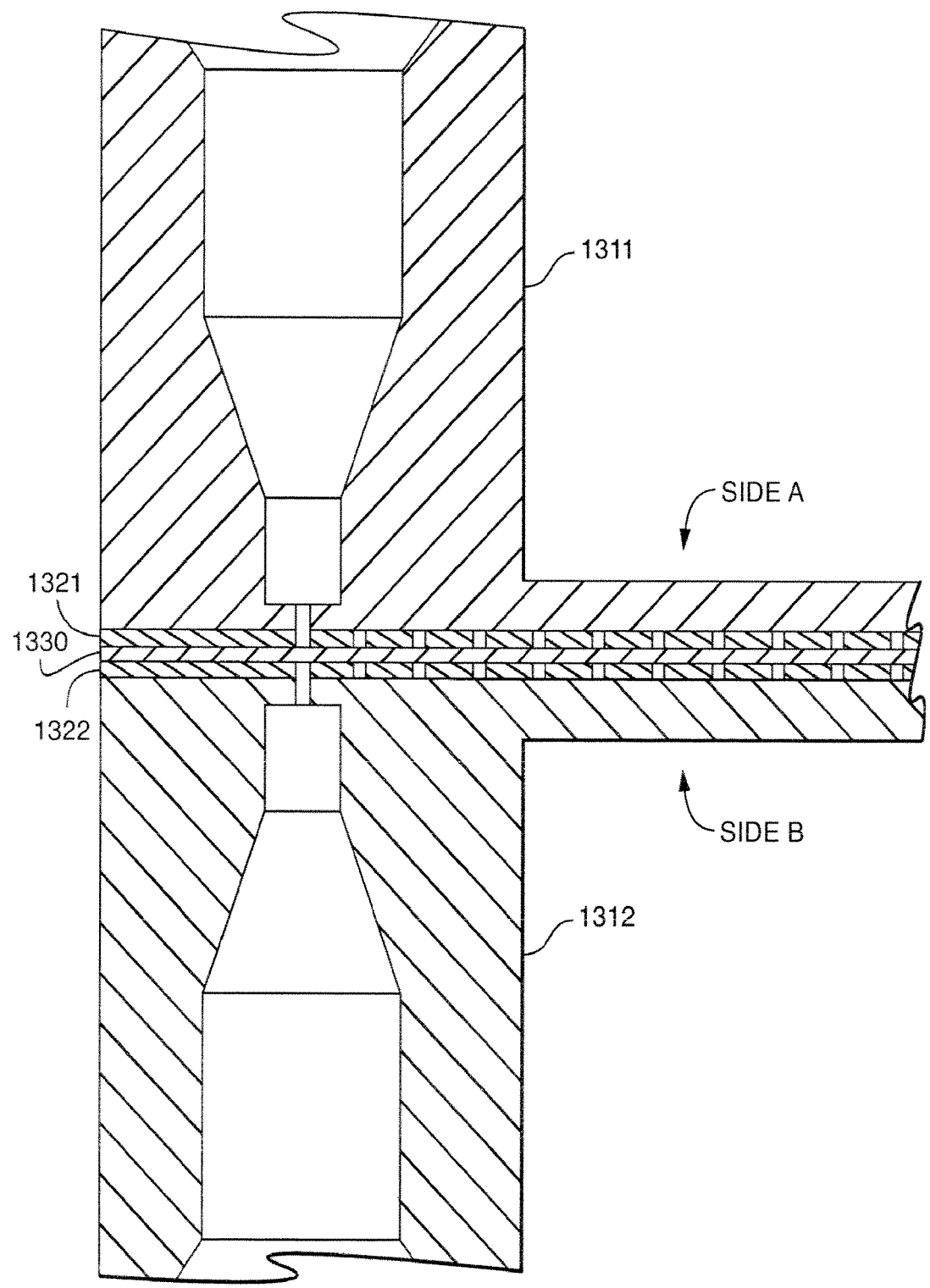
FIG. 10B shows one end of the heat exchanger of FIG. 10A, in greater detail.

FIGS. 10 and 14 are cross-sectional diagrams of illustrative embodiments of diffusion-bonded counter-current heat exchangers 1300, 1400. FIGS. 10A and 10B illustrate a heat exchanger 1300 that provides fluid ports, for two fluid paths, on opposite sides of the exchanger 1300. FIG. 10A is an overall side section view of the exchanger 1300. FIG. 10B shows one end of the heat exchanger 1300, with greater detail.

The exchanger 1300 includes an upper block 1310 that defines inlet and outlet ports for a first fluidic path, a lower block 1312 that defines inlet and outlet ports for a second (counter) fluidic path that is disposed substantially adjacent to the first fluidic path, an upper etched foil 1321 that defines the first fluidic path, a lower etched foil 1322 that defines the second fluidic path, and an intermediate foil 1330 disposed between the etched foils 1321, 1322 to define walls for both fluidic paths. A heated (or cooled) fluid flowing through one of the paths heats (or cools) a fluid flowing in a counter direction through the other path.

The etched foils and associated fluidic paths, in top view, would appear similar to the planar portion 1220 and associated serpentine fluid path illustrated in FIG. 9D.

All components are preferably formed of one of the above described materials, such as titanium, and diffusion bonded to one another, as described above.

Figure 11B:
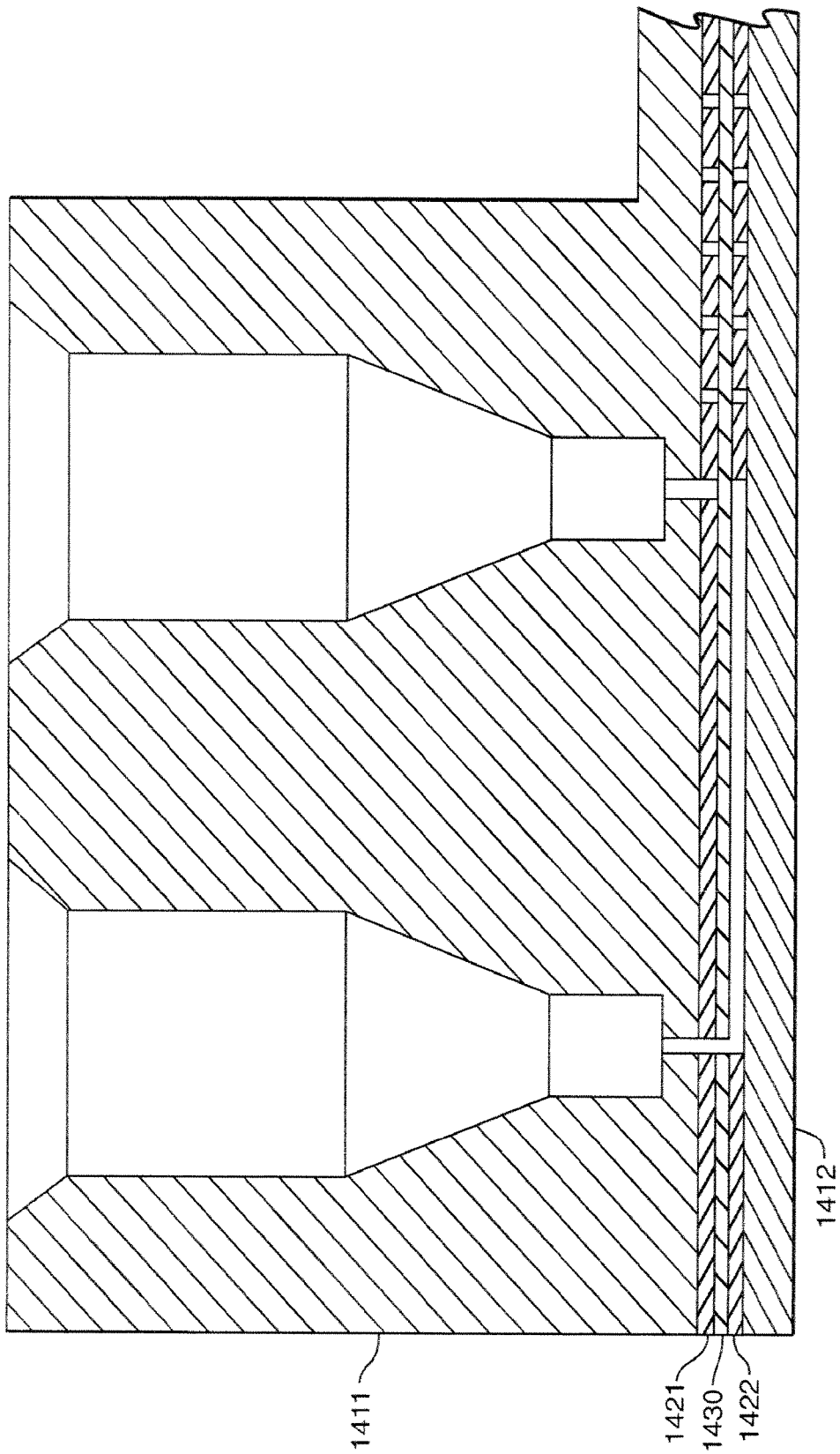
FIG. 11B shows one end of the heat exchanger of FIG. 11A, in greater detail.

FIGS. 11A and 11B illustrate an embodiment of a countercurrent heat exchanger 1400 that is similar in structure to that illustrated in FIGS. 10A and 10B though having all ports defined in an upper block 1411, and thus all ports are on the same side of the exchanger 1400. FIG. 11A is an overall side section view of the exchanger 1400. FIG. 11B is a similar view of the left-most portion of the exchanger 1400, magnified to show greater detail.

The exchanger 1400 includes the upper block 1410 that defines inlet and outlet ports IA, OA for a first fluidic path as well as inlet and outlet ports IB, OB for a second (counter) fluidic path that is disposed substantially adjacent to the first fluidic path, an upper etched foil 1421 that defines the first path, a lower etched foil 1422 that defines the second path, and an intermediate foil 1430 disposed between the etched foils to define walls for both fluidic paths.

The upper foil 1421 and the intermediate foil 1430 define vias to provide fluid communication between the inlet and outlet ends of the lower fluid path and the corresponding inlet and outlet ports IB, OB. The various layers 1411, 1421, 1430, 1422, 1412 are preferably formed from titanium and diffusion bonded.

Figure 12:
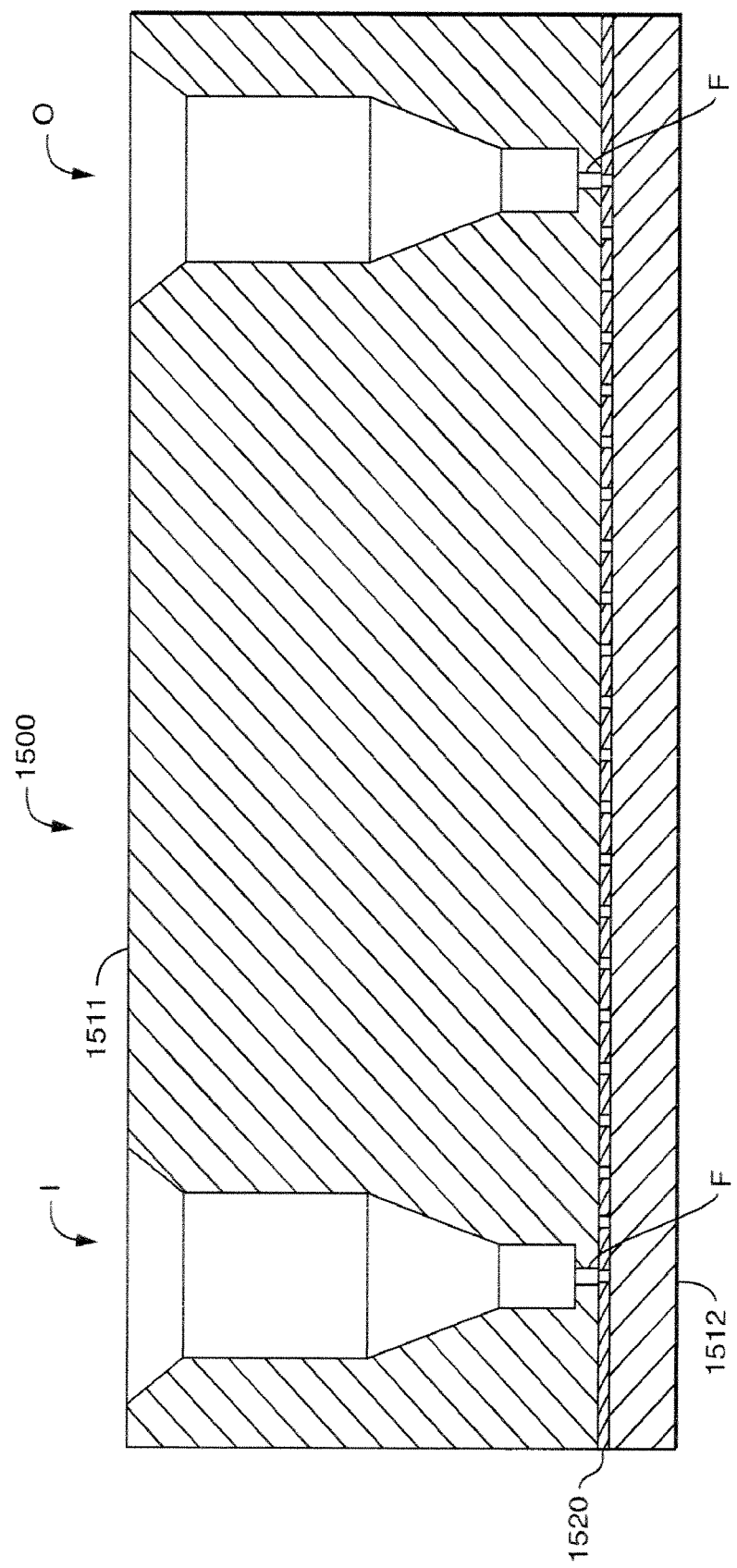
FIG. 12 illustrates in cross section a chromatography separation column unit, in accordance with one embodiment of the invention.

FIG. 12 illustrates in cross section a chromatography separation column unit 1500 implemented via diffusion-bonded titanium. Somewhat similar in construction to the above-described heat exchangers 1200, 1300, 1400, the column unit 1500 includes a lower, unpatterned substrate 1512, a patterned layer 1520 that defines a serpentine column path, an upper block 1511 that defines fluid inlet and outlet ports I, O, and frits F disposed at between the ports I, O and the ends of the serpentine column. The ports I, O are optionally configured to mate with conventional commercially available liquid chromatography plumbing components. For example, the ports I, O optionally are compression ports.

Figure 13:
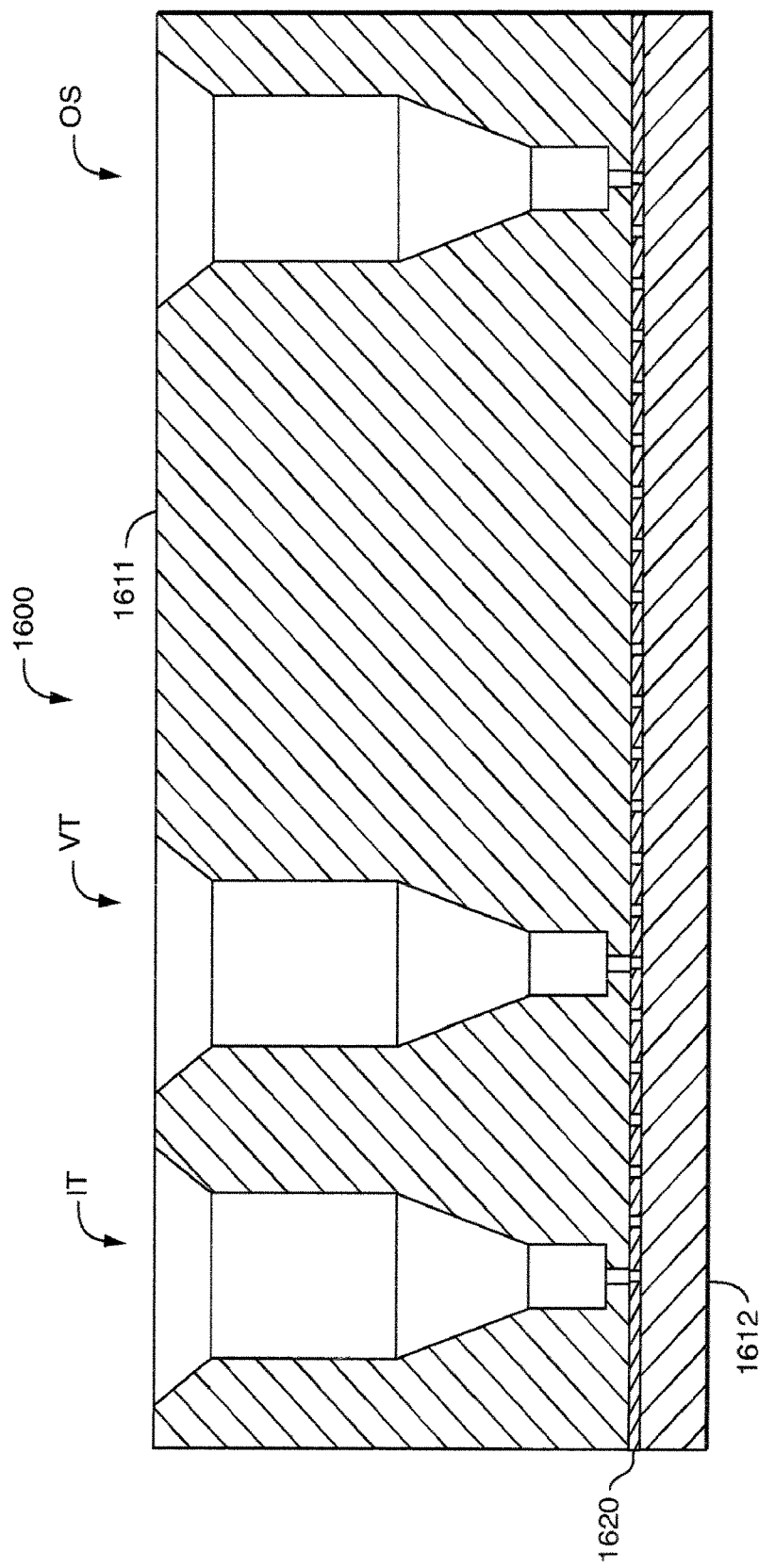
FIG. 13 illustrates in cross section a titanium diffusion-bonded component that includes a trap column and a chromatography separation column, in accordance with one embodiment of the invention.

FIG. 13 illustrates in cross section a titanium diffusion-bonded component 1600 that includes a trap column and a chromatography separation column. The component 1600 includes a substrate 1612, a patterned layer 1620 that defines a serpentine column with a trap column first portion and a separation column second portion, an upper block 1611 that defines a trap column inlet port IT, a trap vent port VT and a separation column outlet port OS, and frits disposed at the base of the ports IT, VT, OS. The ports IT, VT, OS are optionally configured to mate with conventional commercially available liquid chromatography plumbing components.

In some embodiments, planar-implemented separation columns used in high-pressure liquid chromatography (HPLC) or in very-high-pressure liquid chromatography (VHPLC) applications withstand high hydrostatic pressures at least at the 'head' or inlet end of a column. The planar columns are optionally obtained through the use of patterning (such as etching) and bonding techniques described previously, and entail similar structural considerations as for the non-packed fluid conduits and manifolds described elsewhere in this disclosure. The strength and fracture-toughness of titanium (and appropriate alloys of titanium and/or other metal-based materials) are assets in this regard, and provide advantages over some either weaker or more-brittle counterpart materials.

Also notable is the fact that high-pressure-capable compression-fitting ports are optionally incorporated integrally within a titanium planar fluid circuit (as illustrated), allowing the planar-format column to be interfaced-to in a robust manner similar to the manner employed for conventional 4.6 mm or 2.1 mm ID column construction. Currently, capillary or nanoscale columns constructed from materials such as fused-silica capillary present certain difficulties with regard to the implementation of high-pressure connections, and with regard to the installation of frits for retention of a particulate stationary phase packing material. In fully-conventional stainless-steel column construction, a frit is typically engineered as a discrete component which is inserted during column assembly, and which is ruggedly held in place by an end-nut of a column. A bonded-titanium planar column with integral compression-fitting ports, according to some embodiments of the invention, provides a desirable alternative to some conventional approaches.

In an embodiment of a bonded-titanium planar column with integral compression ports, a packing-retaining frit is a discrete component that is loaded into a counterbore (as illustrated above,) and retained in-place by a compression fitting. This assembly step is undertaken prior to column packing, so that at packing time, there is a robust and reliable frit present for retention of the packing material. The loads imposed upon a frit during an initial phase of column packing may be very significantly greater than the loads that the frit sees during normal column operation with the column-bed fully in-place. Some alternative frit implementations known for fused-silica capillary columns at times fail (with the frit being expelled) during a typically aggressive phase of operation used to pack a column.

Alternately, a frit is generated within a bore of a connecting capillary tube that receives an outlet flow from a column. Such a frit is optionally constructed by thermal sintering of glass microspheres within the bore of the capillary, or by the in-situ reaction of a silicate. In either case, the fritted tube is then inserted into the compression port at the intended outlet end of the planar column, and is mechanically retained in the port in, for example, a conventional way by the action of a compression screw on a ferrule.

The implementation of inlet frits is optionally accomplished in substantially the same way, as a similar compression-fitting port optionally exists at an inlet end of a column. Typically, the inlet frit is installed only after the column bed has been packed. The provision of an inlet frit (as per some conventional column construction) imparts some increased column robustness relative to columns that have only an outlet frit, and that are fully unprotected at the inlet end.

It will be recognized that the techniques described above to implement a single chromatography column within a single diffusion-bonded titanium structure are advantageously applied to implement multiple columns (such as a trapping column in conjunction with an analytical column) within a diffusion-bonded titanium structure. The fluidic routing options that exist in a planar fluid circuit may be used advantageously to appropriately fluidically interconnect the two or more columns to achieve the desired functionality.

Additional compression-fitting ports may be machined into the structure as necessary, and individually those ports may include, or may not include, provisions for fritting as appropriate to the intended functioning of the device. The illustrative embodiment shown above incorporates a trapping column and an analytical column and fluidic ports within a single diffusion-bonded structure. In many preferred implementations, the trapping column bed will be shorter and of wider cross-section than the analytical column bed. This variation in the relative dimensions of the columns is optionally accomplished by control of etching in these two distinct regions. While the exemplary embodiment depicts two columns, any number of columns are contemplated within the scope of the present invention.

Some aspects of the invention allow diffusion-bonded components to contribute to a useful and fully-integrated internal component of a mechanical device such as a metallic high-pressure valve stator, as discussed next.

Figure 14A:
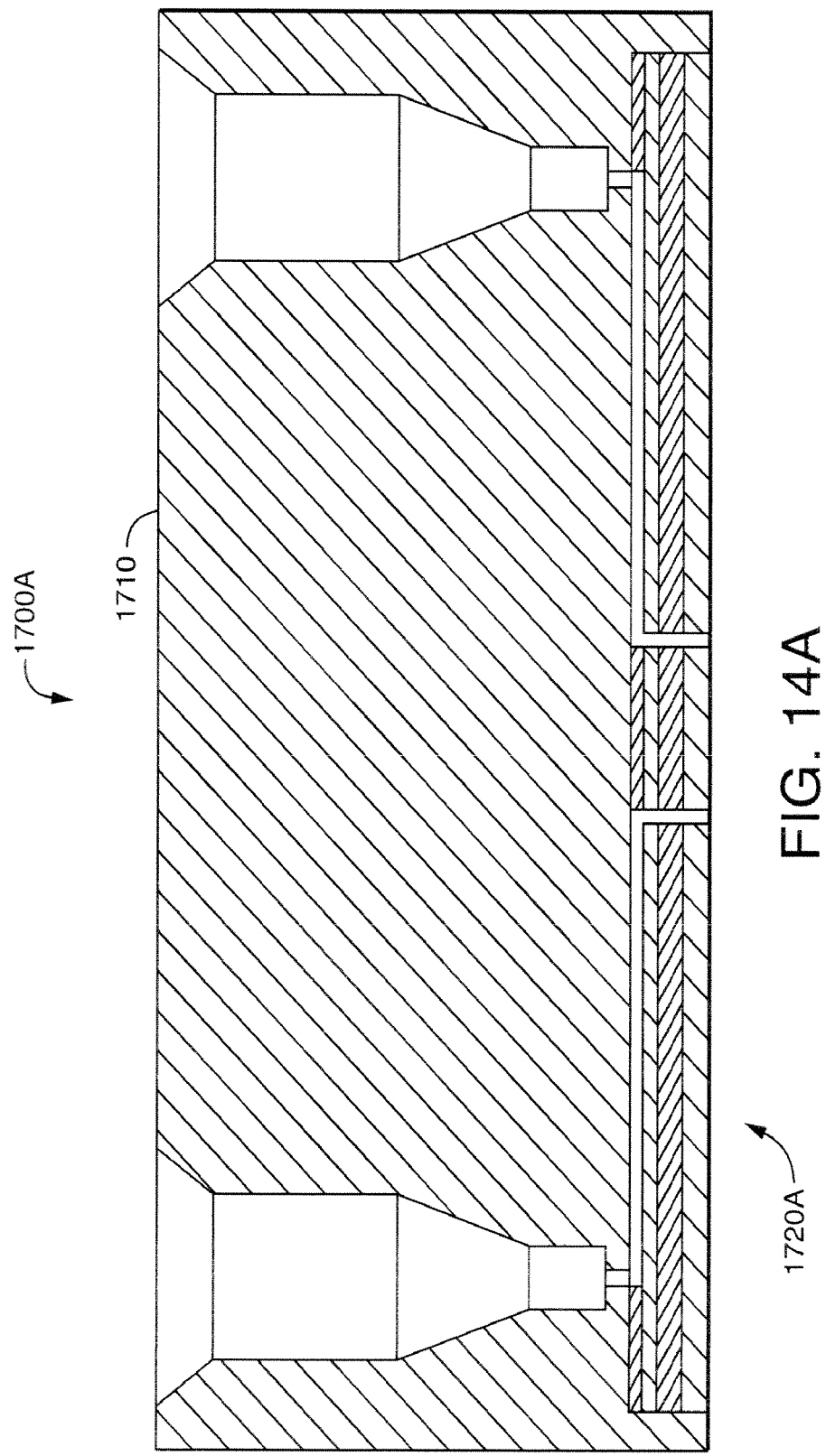
FIG. 14A illustrates, in cross section, a diffusion-bonded stator assembly at an intermediate stage of fabrication, in accordance with one embodiment of the invention.
Figure 14B:
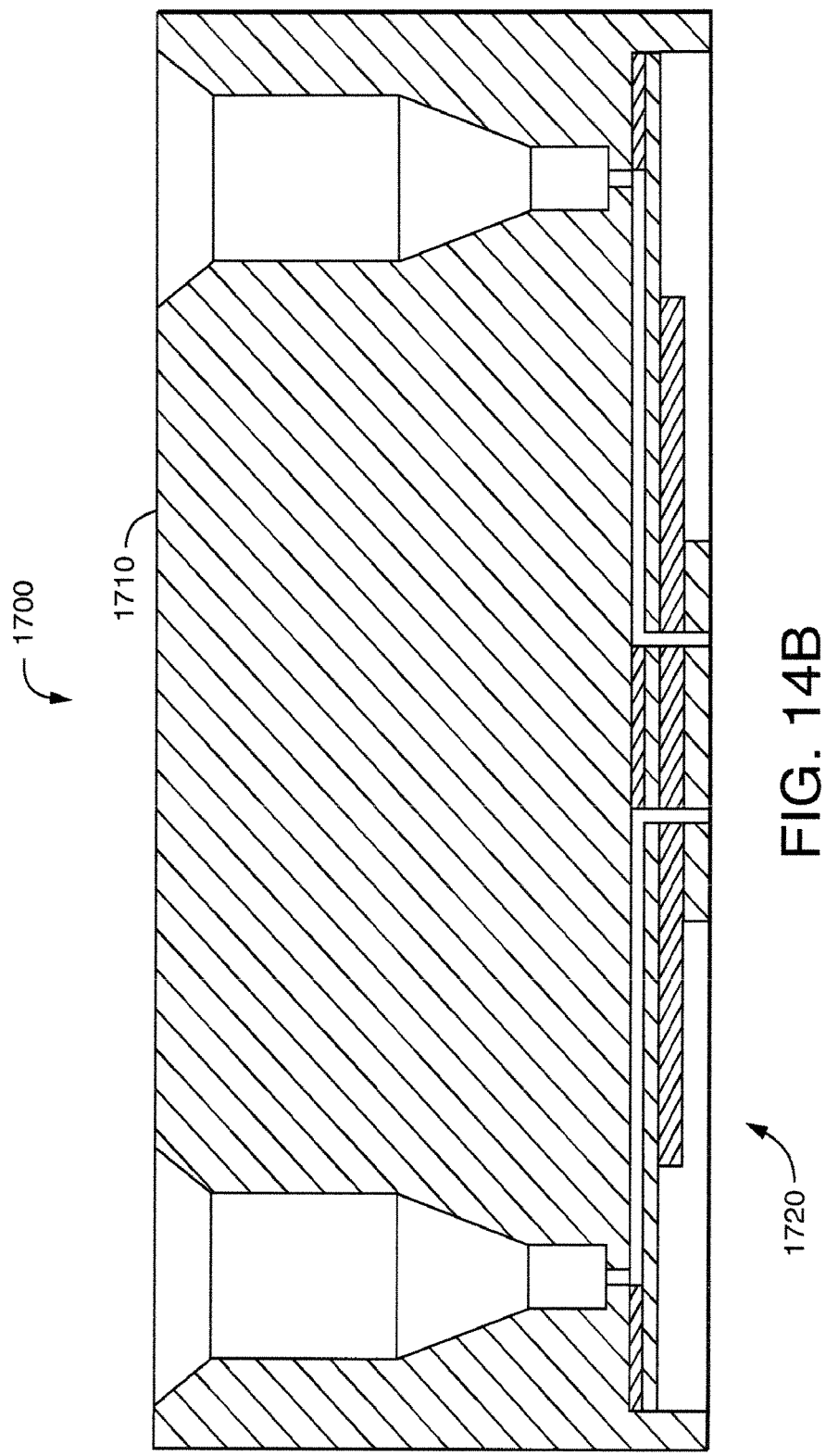
FIG. 14B illustrates the completed diffusion-bonded stator assembly of FIG. 14A.
Figure 14C:
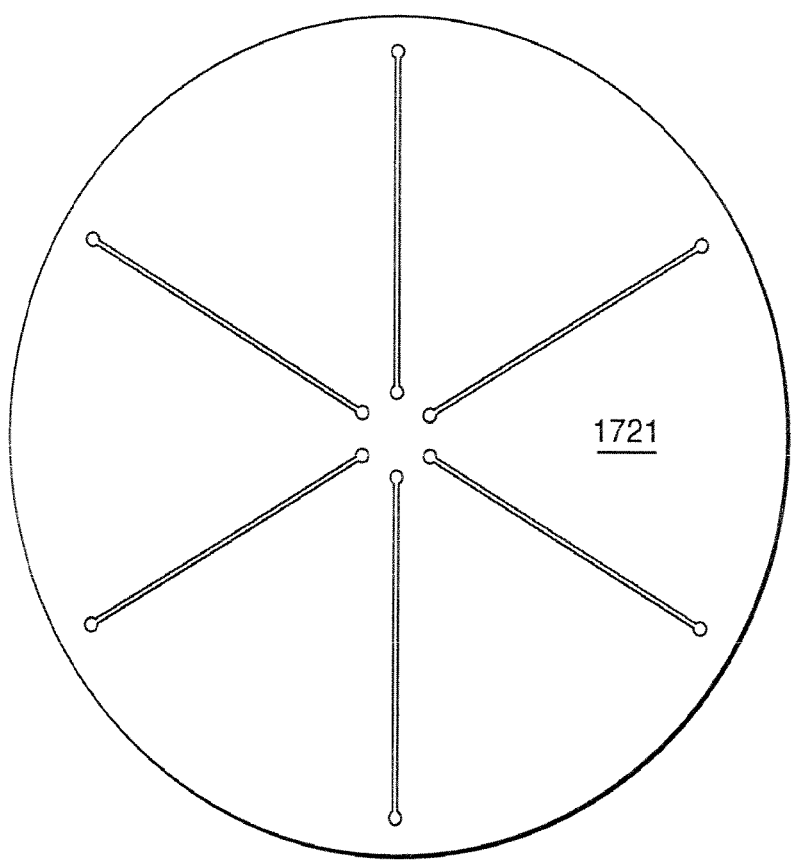
FIG. 14C, is a top view of a gasket of the stator assembly of FIGS. 14A and 14B.

FIG. 14A illustrates, in cross section, an incomplete diffusion-bonded stator assembly 1700A (i.e., at an intermediate stage of fabrication) and FIG. 14B illustrates a completed diffusion-bonded stator assembly 1700 of a very high-pressure (VHP) rotary shear-seal valve. The stator assembly 1700 is used, for example, in place of a conventionally-machined VHP valve stator, as will be understood by one having ordinary skill in the liquid-chromatography arts. The stator assembly 1700 is formed from titanium and includes an external-interface portion 1710 that defines two or more ports, such as compression ports (as illustrated,) and a rotor-interface portion 1720 (an incomplete portion 1720A is shown in FIG. 14A) having a surface configured to mate with a rotor (not shown) of the rotary-shear-seal valve. The rotor-interface portion 1720 includes fluid paths, one associated with each compression port in the external-interface portion 1710. The stator assembly 1700 provides improved location of compression ports relative to the critical stator-rotor sealing area.

The rotor-interface portion 1720 is formed from at least one layer, which is diffusion bonded to the external-interface portion 1710. In the illustrated example, the rotor-interface portion 1720 includes four diffusion-bonded layers, including a gasket 1721 (illustrated, top view, in FIG. 14C.) The gasket 1721 is patterned to define the fluid paths associated with the ports. In this example embodiment, the gasket 1721 defines six fluid paths, and the external-interface portion 1710 has six compression ports, of which two are shown in FIGS. 14A and 14B. The six ends of the fluid paths are connected to the surface of the rotor-interface portion 1720 through six vias extending through the remaining three layers.

As illustrated in FIG. 14A, the four layers of the incomplete rotor-interface portion 1720A are diffusion bonded to the external-interface portion 1710 prior to final removal of material from the bonded four layers. FIG. 14B illustrates the layers after material removal. The final configuration provides a stator surface for the stator assembly 1700 that suitably matches a corresponding surface of a rotor of the rotary shear-seal valve.

Some prior art stators are fabricated by machining stainless-steel bar stock. A valve stator is a relatively complex machined part, which includes, for example, compression ports for six external tubing connections, each of which terminates very close to the valve stator-rotor sealing interface. The flatness and surface finish of the stator-rotor sealing interface are both typically critical to achieving a high-performance (low-leakage) seal that will endure hundreds of thousands of valve actuations.

In some prior valves, the proximity of the compression port details to the stator-rotor sealing interface in combination with excessive wrench-tightening of compression screws at times causes localized distortion of the sealing interface, resulting in an excessive valve leakage rate and reduced valve lifetime. In addition, in the interest of valve cycle lifetime, attributes of a relatively soft valve rotor material make it desirable to through-connect the external compression ports to the stator-rotor sealing plane with carefully-deburred drilled holes as small as 0.004" diameter or better. The drilling and deburring of such small holes, while maintaining critical feature positioning and internal alignments, is non-trivial.

In some embodiments of the invention, such as the diffusion-bonded stator assembly 1700, an etched-and-bonded fluid circuit element is usefully integrated into a machined stator component for the purpose of bridging between a more macroscopic mechanically-machined external plumbing interface and a more microscopic internal structure interfacing to a rotor. The etched-and-bonded fluid circuit allows external compression fitting ports to be located at positions radially-displaced away from the critical central region of the valve encompassing the stator-rotor sealing interface. This radially-displaced positioning removes to a safe peripheral region the stresses and material strain associated with, for example, ferrules and screws, while simultaneously permitting easier access to individual compression fittings.

A fluid path, as defined, for example, by the gasket 1721, efficiently conveys fluid between the peripheral ports and the critical central region of a valve. Substantially burr-free apertures are produced with exceptionally good positional reproducibility, characteristic of artwork-based etching. Once bonded in place, a fluid circuit so used is an integral, and not-readily-distinguishable, part of a titanium valve stator having a conventionally-machined external appearance.

Some embodiments of the invention include a coating on walls that define one or more fluid paths. For example, passivation of a clean titanium surface is optionally provided by exposure to oxygen, resulting in the formation of a surface layer of titanium dioxide ($TiO_2$), which, in some cases, is effective in preventing corrosion of the underlying metal. Alternative embodiments include the formation of surface layers that avoid the exposure of $TiO_2$ to the solvent wetted path. One such surface layer is titanium nitride (TiN), optionally deposited in any suitable process, including known processes.

A TiN coating is optionally applied using a PVD process (Physical Vapor Deposition.) To improve surface coverage using a titanium substrate, in some embodiments, a TiN coating is formed by an in-situ reaction. This reaction involves the flow of a high-purity nitrogen gas stream over the titanium surface, and the application of heat to achieve an elevated substrate temperature near the annealing temperature. Since some embodiments of a microfluidic device convey fluid through an internal 'wetted path', a nitrogen stream is optionally provided, for example, using 1/16" OD chromatography tubing interfacing to an appropriate inlet and outlet port(s) to convey the nitrogen gas through the device. A suitable device temperature is optionally maintained using a vacuum oven and related fixturing as employed for a diffusion bonding process itself.

Alternatives to TiN coatings include, for example, TiCN (titanium carbo-nitride) and TiAlN (titanium aluminum nitride).

Surface layers are optionally produced prior to bonding. In some preferred embodiments, surface layers are produced after bonding, for example, to avoid interfering with the bonding process.

Some embodiments employ diamond or diamond-like coatings for, for example, a valve stator application. In the case of a valve stator, a coating optionally is formed on an open/exposed stator surface in a commercial microwave-enhanced PVD device. Other areas of the valve stator are optionally masked (for example, masked in a relatively coarse manner appropriate to that application.)

In view of the above description, one having ordinary skill in separation science will recognize that numerous alternative embodiments of fluidic circuits are within the scope of the invention. For example, additional embodiments of the invention relate to improved liquid chromatography systems that have fluidic components with reduced size, fewer connections, smaller size, increased integration and/or other features, relative to some prior HPLC systems.

For example, one embodiment involves a solvent pump of reduced size relative to prior chromatography solvent pumps. Such a pump could suitably be used for the pump 120 illustrated in FIG. 1. The pump provides reduced spacing of the pump's cylinders; in some prior pumps the spacing is constrained, at least in part, by accessibility requirements for plumbing the heads with discrete tubing (for example, providing wrench access to compression screws at each end of each tube, and providing for generous bend radii so that tubes do not become kinked when they are inserted or removed from relatively deep compression-fitting ports).

Accordingly, in one pump embodiment, a diffusion-bonded titanium manifold subassembly mounts the pump heads in relatively very close proximity to one another, with the intervening plumbing paths implemented in substantially planar form on the titanium subassembly. Optionally, titanium cylinder heads are not diffusion bonded directly onto a titanium substrate, to provide head removal to access piston seals (optionally, a normal service requirement.) Thus, the piston seals are also optionally protected from a titanium diffusion-bonding temperature cycle.

On the inlet side of the pump, a titanium subassembly optionally implements a degasser function and/or incorporates or integrates a manifold of a gradient proportioning valve. Valve solenoids are optionally mounted directly to a titanium substrate, as well as diaphragms used for decoupling a fluid inertance of long solvent-reservoir lines from the pump intake. An intake assembly, according to one embodiment of the invention, is smaller and less prone to leakage, with the elimination of many discrete tubes.

The two above-described titanium are optionally separate and distinct, or are integrated into a single unit, based on packaging constraints.

In some embodiments of the invention, metal foils are patterned through use of high-vacuum electron-beam cutting (HV-EBC), with or without the use of a highly-localized process-gas to enhance the volatilization and removal of metal from a fusion site. For example, a programmable, steered-beam (or beam-deflection) mode of HV-EBC is suitable for patterning a titanium foil without requiring a patterned mask. In some cases, however, a mask material is utilized to limit substrate damage which may occur adjacent to the beam path.

Commercially available electron-beam sources employed in high-vacuum systems exist across many orders of beam-current magnitude, ranging from extremely narrow (few-nanometer diameter) picoAmpere (pA) beams characteristic of electron microscopy, to relatively massive beams used to perform process metal-melting or vacuum evaporation (to 150 kW), or to achieve the penetration needed to butt-weld thick sections (multiple inches) of steel. Generally, reducing beam diameter also reduces beam current; for commercially-viable metal-foil cutting, one preferably selects a beam diameter that is narrow enough to generate the required feature detail in the substrate, while still having sufficient current available to rapidly fuse a thin metal foil. Such beams may be employed for high-vacuum electron-beam welding (HV-EBW.)

Known systems for HV-EBW typically include a vacuum chamber of sufficient size to encompass a workpiece, the workpiece-holder/stage, and the beam-path, and incorporate programmable controls for beam-deflection, with or without programmed stage motion. Known systems at times incorporate a relatively shallow convergence-angle for the beam, such that the heated path through the substrate is relatively straight-sided (i.e., the taper of the beam is negligible over the thickness of an intended metal-foil substrate.) The beam rate-of-advance, the beam-current, beam quality, the heat-capacity and thermal conductivity of the metal foil, and the incorporation of a process gas, collectively impart a quality to the surface being machined, with a goal to minimize the extent of production of vertical striations or other defects in the machined surface. HV-EBC of titanium, in the absence of a reactive process-gas, is also a potentially clean alternative relative to reactive-ion etching (RIE).

Some embodiments employ other steered-beam techniques, such as the above-mentioned FIB milling. Generally, though FIB milling, with or without the use of a reactive process-gas to enhance volatilization (or to reduce re-deposition) of sputtered material, while providing exceptionally fine resolution and smoothly-cut surfaces, is not fast enough with commercially available machines to be a viable commercial alternative to RIE or to wet-etching for constructing chromatography components.

Various illustrative implementations of the present invention may be applied to a variety of systems and/or methods involving fluid transport. As used herein, the terms "fluid", "fluidic" and/or any contextual, variational or combinative referent thereof, are generally intended to include anything that may be regarded as at least being susceptible to characterization as generally referring to a gas, a liquid, a plasma and/or any matter, substance or combination of compounds substantially not in a solid or otherwise effectively immobile condensed phase. The terms "inlet" and "outlet" are generally understood to refer to any cross-sectional area or component feature of a device, the flux through which tends to translate fluid from a volume element substantially external/internal to a device or component to a volume element substantially internal/external to the device or component.

Variations, modifications, and other implementations of what is described herein will occur to those of ordinary skill in the art without departing from the scope of the invention as claimed. For example, some embodiments include one or more of the following components: a detector cell end-structure; a mass-spectrometer interface cone providing, for example, paths for nebulization gas, desolvation gas, etc.; a diffusion-bonded intake manifold for a pump, including, for example, a planar gas-exchange element and/or a gradient mixer; a diffusion bonded manifold for between-cylinder and/or post-cylinder of a pump for, for example, cost and size reduction; and a planar consolidated manifold for an autosampler for, or example, cost and size reduction. Some embodiments include, for example, any one or a combination of the following features: two or more separation columns; two or more trap columns; a metallic substrate that includes check valve(s), pump(s), and/or electronic devices such as memory devices, identification devices (such as A RFID), and/or display devices. Moreover, some integrated metal-based devices including these features are suitable for use as consumable devices, due to low manufacturing cost. Accordingly, the invention is to be defined not by the preceding illustrative description but instead by the scope of the following claims.

What is claimed is:

1. A rotary-shear-seal valve, comprising:
a stator assembly comprising
an external-plumbing interface portion comprising titanium, and defining at least two tubing ports; and a gasket comprising titanium and diffusion bonded to the external-plumbing interface portion, wherein the gasket defines a fluid circuit for each of the tubing ports, an outer end of each fluid circuit being in fluid communication with a corresponding one of the tubing ports, the fluid circuits including a titanium surface layer coating comprising at least one of TiN, TiCN, or TiAlN along walls that define one or more fluid paths.

2. The valve of claim 1, further comprising a rotor-interface portion comprising titanium and having a surface configured to mate with a rotor of the valve, wherein the rotor-interface portion is diffusion bonded to the gasket and defines a fluid via for each of the fluid circuits, each fluid via in fluid communication with an inner end of its corresponding fluid circuit.

3. The valve of claim 2, wherein the rotor-interface portion comprises at least two diffusion-bonded layers.

4. The valve of claim 1, wherein the external-plumbing interface portion defines six tubing ports, and the gasket defines six fluid circuits for the six tubing ports.

5. The valve of claim 1, further comprising a diamond-like coating on an exposed stator surface.

\* \* \* \* \*